(12) United States Patent
Mouillon et al.

(10) Patent No.: US 11,667,922 B2
(45) Date of Patent: Jun. 6, 2023

(54) FUNGAL CHAPERONE PROTEINS

(71) Applicant: Novozymes A/S, Bagsvaerd (DK)

(72) Inventors: Jean-Marie Mouillon, Sodra Sandby (SE); Pernille Hvid Christensen, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 17/040,906

(22) PCT Filed: Mar. 25, 2019

(86) PCT No.: PCT/EP2019/057416
§ 371 (c)(1),
(2) Date: Sep. 23, 2020

(87) PCT Pub. No.: WO2019/185535
PCT Pub. Date: Oct. 3, 2019

(65) Prior Publication Data
US 2021/0010010 A1 Jan. 14, 2021

(30) Foreign Application Priority Data

Mar. 26, 2018 (EP) ..................................... 18163921

(51) Int. Cl.
*C12N 15/80* (2006.01)
(52) U.S. Cl.
CPC .................................. *C12N 15/80* (2013.01)
(58) Field of Classification Search
None
See application file for complete search history.

(56) References Cited

U.S. PATENT DOCUMENTS

2019/0048380 A1* 2/2019 Kim ..................... C12N 9/0071

FOREIGN PATENT DOCUMENTS

| DE | 102010016387 | 10/2011 |
|----|---|---|
| WO | 1994019471 A1 | 9/1994 |
| WO | 2004067709 A2 | 8/2004 |
| WO | 2005061718 A1 | 7/2005 |
| WO | 2005061719 A1 | 7/2005 |
| WO | 2006067511 A1 | 6/2006 |
| WO | 2017112847 A1 | 6/2017 |

OTHER PUBLICATIONS

Solis et al., "Defining the Essential Function of Yeast Hsf1 Reveals a Compact Transcriptional Program for Maintaining Eukaryotic Proteostasis", Molecular Cell, 2016, vol. 63, pp. 60-71; Supplementary Information, pp. 1-39. dx.doi.org/10.1016/j.molcel.2016.05.014.*
Abrams et al, 2014, The J Of Biological Chem 289(19), 13155-13167.
Borkovich et al, 1989, Mol Cell Biol 9(9), 3919-3930.
Brown et al, 2000, The journal of cell biology 150(1), 65-76.
Burgraaf et al, 2016, FEMS Microbiol Lett 363, 1-7.
Conesa et al, 2001, Fungal Gen Biol 33, 155-171.
Cowen et al, 2005, Science 309, 1-19.
Hideyuki et al, 1993, Gene 132(1), 57-66.
Kandasamy et al, 2018, J Cell Sci 131(6), 1-11.
Kideyuki et al, 1993, Gene 132(1), 57-66.
Kwon et al, 2017, Biochem Biophys Res Com 493, 481-486.
Roberts et al, 2004, Yeast 21(2), 107-117.
Verghese et al, 2012, Microbiol Mol Biol Revs 76, 115-158.
Westers et al, 2004, Biochim Biophys Acta 1694(1-3), 299-310.

* cited by examiner

*Primary Examiner* — Suzanne M Noakes
(74) *Attorney, Agent, or Firm* — Eric J. Fechter

(57) ABSTRACT

The present invention relates to fungal host cells comprising nucleic acid constructs comprising a heterologous promoter operably linked to polynucleotidea encoding a chaperone, nucleic acid constructs comprising a polynucleotide encoding a chaperone, and methods for producing polypeptides of interest.

18 Claims, 15 Drawing Sheets

Specification includes a Sequence Listing.

SEQUENCE LISTING

<160> NUMBER OF SEQ ID NOS: 25

<210> SEQ ID NO 1
<211> LENGTH: 2044
<212> TYPE: DNA
<213> ORGANISM: Aspergillus oryzae

<400> SEQUENCE: 1 atggccccg ctgtcggtat cgatttgggt accacctact cctgtgtggg tgtgttccgt    60

-continued

```
gatgaccgca ttgaaatcat tgccaacgac cagggtaacc gtaccacccc ttccttcgtg    120
gctttcaccg ataccgagcg tctcatcggt gatgccgcca agaaccaggt cgcaatgaac    180
cctcacaaca ctgtcttcga tgccaagcgt ctgatcggtc gtcgttatgc cgatgctgag    240
gtccagtctg atatgaagca ctggcccttc aagatcgtcg ataagggtgg caagcccatc    300
atccaggttg agttcaaggg cgaagagaag caattcactc ccgaggaagt ctcctctatg    360
gtcctgacca agatgcgtga gaccgcagag gcctatcttg tggtactgtg taacaacgcc    420
gttatcactg tccccgccta cttcaacgac tcccagcgtc aggctaccaa ggatgctggt    480
ctcatcgccg gtctgaacgt cctccgtatc attaacgagc ccactgccgc cgccatcgcc    540
tacggtctag acaagaaggc cgagggcgag cgcaatgtcc tgatcttcga tttgggtggt    600
ggtacctttg atgtttctct cttgaccatt gaagaaggta tcttcgaggt caaggctacc    660
gctggtgaca ctcaccttgg tggtgaggac ttcgacaacc gtctcgtcaa ccatttcgtt    720
aacgagttca acgcaagca caagaaaggt tggtcttttg attccgataa tcgcaaagcc    780
cccaatgcta acttggatat gacagatctc actaccaacg cgcgtgccct ccgccgtctc    840
cgcactgcct gtgagcgtgc caagcgtaca ctgtcttctg ctgcccagac tctattgaa    900 atcgactctc tctttgaggg tattgatttc tatacctcga tcacccgtgc ccgtttcgag    960
gaactttgcc aggacctctt ccgcggtact atggagcctg tcgagcgtgt cctccgtgat    1020
gccaagatcg acaagtcctc tgtccacgag attgtcctgg tcggtggctc taccgtatc    1080 cccaagatcc agcgccttgt ctccgatttt ttcaacaagg agcccaacaa gtccatcaac    1140
cccgatgagg ccgttgccta cggtgctgcc gttcaggctg ccatcctgtc cggtgatagt    1200
tcctccaagt ccaccaacga gatcctgcta ctcgacgttg ccccctgtc tctcggtatc    1260 gaaaccgctg gtggtgtcat gaccgctcta atcaagcgca acaccacaat tcccaccaag    1320
aagtccgaga ctttctccac ttactctgac aaccagcctg gtgtgttgat ccaggtttac    1380
gagggtgaac gtgctcgtac taaggacaac aacctgctcg gaaagttcga gctcactggc    1440
attcctcccg ctccccgtgg tgttcctcag atcgaggtta ccttcgatgt cgatgccaac    1500
ggtatcatga acgtttctgc cgtcgagaag ggcactggaa agaccaacaa gatcaccatc    1560
accaacgaca agggccgtct ctccaaggag gagattgagc gcatgcttgc cgatgccgag    1620
aagtacaagg ctgaggatga ggctgaggct cccgtatcc aggccaagaa cggccttgag    1680
tcttatgcct actccctcaa gaacaccatc agcgagggca agcttaccat ctctgactcc    1740
gacaaggaga aggtcaccag caaggttgat gagatcatcg ttggcttga cagcaaccag    1800 accgccacca aggaggagta cgagtctcag cagaaggagc tcgaagggta tgtgatatga    1860 aaccccttt atccctccat gactaatatg atgctaactg tgcgctagtg ttgccaaccc    1920
tatcatctcc gctgcttatg gcggtgccgc tggtgctgct cctggcggtg ctcccggcgc    1980 tgccccggt ggctccactc gcaccgctga cgaggttgag gagaagcccg aggagcttga    2040
ctaa                                                              2044
```

<210> SEQ ID NO 2
<211> LENGTH: 641
<212> TYPE: PRT
<213> ORGANISM: Aspergillus oryzae

<400> SEQUENCE: 2

Met Ala Pro Ala Val Gly Ile Asp Leu Gly Thr Thr Tyr Ser Cys Val
1               5                   10                  15

```
Gly Val Phe Arg Asp Asp Arg Ile Glu Ile Ala Asn Asp Gln Gly
         20                  25                  30

Asn Arg Thr Thr Pro Ser Phe Val Ala Phe Thr Asp Thr Glu Arg Leu
         35                  40                  45

Ile Gly Asp Ala Ala Lys Asn Gln Val Ala Met Asn Pro His Asn Thr
 50                  55                  60

Val Phe Asp Ala Lys Arg Leu Ile Gly Arg Arg Tyr Ala Asp Ala Glu
 65                  70                  75                  80

Val Gln Ser Asp Met Lys His Trp Pro Phe Lys Ile Val Asp Lys Gly
             85                  90                  95

Gly Lys Pro Ile Ile Gln Val Glu Phe Lys Gly Glu Glu Lys Gln Phe
             100                 105                 110

Thr Pro Glu Glu Val Ser Ser Met Val Leu Thr Lys Met Arg Glu Thr
             115                 120                 125

Ala Glu Ala Tyr Leu Gly Gly Thr Val Asn Asn Ala Val Ile Thr Val
 130                 135                 140

Pro Ala Tyr Phe Asn Asp Ser Gln Arg Gln Ala Thr Lys Asp Ala Gly
145                 150                 155                 160

Leu Ile Ala Gly Leu Asn Val Leu Arg Ile Ile Asn Glu Pro Thr Ala
             165                 170                 175

Ala Ala Ile Ala Tyr Gly Leu Asp Lys Lys Ala Glu Gly Glu Arg Asn
             180                 185                 190

Val Leu Ile Phe Asp Leu Gly Gly Gly Thr Phe Asp Val Ser Leu Leu
             195                 200                 205

Thr Ile Glu Glu Gly Ile Phe Glu Val Lys Ala Thr Ala Gly Asp Thr
             210                 215                 220

His Leu Gly Gly Glu Asp Phe Asp Asn Arg Leu Val Asn His Phe Val
225                 230                 235                 240

Asn Glu Phe Lys Arg Lys His Lys Lys Asp Leu Thr Thr Asn Ala Arg
             245                 250                 255

Ala Leu Arg Arg Leu Arg Thr Ala Cys Glu Arg Ala Lys Arg Thr Leu
             260                 265                 270

Ser Ser Ala Ala Gln Thr Ser Ile Glu Ile Asp Ser Leu Phe Glu Gly
             275                 280                 285

Ile Asp Phe Tyr Thr Ser Ile Thr Arg Ala Arg Phe Glu Glu Leu Cys
             290                 295                 300

Gln Asp Leu Phe Arg Gly Thr Met Glu Pro Val Glu Arg Val Leu Arg
305                 310                 315                 320

Asp Ala Lys Ile Asp Lys Ser Ser Val His Glu Ile Val Leu Val Gly
             325                 330                 335

Gly Ser Thr Arg Ile Pro Lys Ile Gln Arg Leu Val Ser Asp Phe Phe
             340                 345                 350

Asn Lys Glu Pro Asn Lys Ser Ile Asn Pro Asp Glu Ala Val Ala Tyr
             355                 360                 365

Gly Ala Ala Val Gln Ala Ala Ile Leu Ser Gly Asp Ser Ser Ser Lys
             370                 375                 380

Ser Thr Asn Glu Ile Leu Leu Leu Asp Val Ala Pro Leu Ser Leu Gly
385                 390                 395                 400

Ile Glu Thr Ala Gly Gly Val Met Thr Ala Leu Ile Lys Arg Asn Thr
             405                 410                 415

Thr Ile Pro Thr Lys Lys Ser Glu Thr Phe Ser Thr Tyr Ser Asp Asn
             420                 425                 430
```

| | | | | | | | | | | | |
|---|---|---|---|---|---|---|---|---|---|---|---|
|Gln|Pro|Gly|Val|Leu|Ile|Gln|Val|Tyr|Glu|Gly|Glu|Arg|Ala|Arg|Thr|
| |435| | | |440| | | |445| | |

Lys Asp Asn Asn Leu Leu Gly Lys Phe Glu Leu Thr Gly Ile Pro Pro
    450                 455                 460

Ala Pro Arg Gly Val Pro Gln Ile Glu Val Thr Phe Asp Val Asp Ala
465                 470                 475                 480

Asn Gly Ile Met Asn Val Ser Ala Val Glu Lys Gly Thr Gly Lys Thr
            485                 490                 495

Asn Lys Ile Thr Ile Thr Asn Asp Lys Gly Arg Leu Ser Lys Glu Glu
                500                 505                 510

Ile Glu Arg Met Leu Ala Asp Ala Glu Lys Tyr Lys Ala Glu Asp Glu
            515                 520                 525

Ala Glu Ala Ser Arg Ile Gln Ala Lys Asn Gly Leu Glu Ser Tyr Ala
    530                 535                 540

Tyr Ser Leu Lys Asn Thr Ile Ser Glu Gly Lys Leu Thr Ile Ser Asp
545                 550                 555                 560

Ser Asp Lys Glu Lys Val Thr Ser Lys Val Asp Glu Ile Ile Gly Trp
                565                 570                 575

Leu Asp Ser Asn Gln Thr Ala Thr Lys Glu Glu Tyr Glu Ser Gln Gln
            580                 585                 590

Lys Glu Leu Glu Gly Val Ala Asn Pro Ile Ile Ser Ala Ala Tyr Gly
    595                 600                 605

Gly Ala Gly Ala Ala Pro Gly Gly Ala Pro Gly Ala Ala Pro Gly
    610                 615                 620

Gly Ser Thr Arg Thr Ala Asp Glu Val Glu Glu Lys Pro Glu Glu Leu
625                 630                 635                 640

Asp

<210> SEQ ID NO 3
<211> LENGTH: 2495
<212> TYPE: DNA
<213> ORGANISM: Aspergillus oryzae

<400> SEQUENCE: 3
atgagtgtag ttggaatcga cttcggtgcc cagagcacca agattggtgt cgcccgtaat    60
aagggtatcg acattgtgcg tatcatgcct tccccacctt cagcgcttcc ctatactttt   120
ttttttctta ccaaccccgt cacttgaacc attttgaaat gcaaagacta accgtcggtg   180
cgactcaatt tagatcacca acgaagtttc aacagatct actccgtatg tccacccctc    240
tgttaagatt ccgccccacc ccagccaaca acgagcttaa cggcgtgggt tttatctagc   300
catcctatac tgactgtgtg tgatgttcag ctccctcatc tccttcgaca caaatgtag    360 atatctcggt gaggctgcta agacacgaga gacctccaac ctgaagaaca ctgttgcaaa   420
cctcaagcgc tgattggcc gctcattcag cgaccctgat gttcagatcg agcagagctt    480
caatactgct actctctgcg atgtgaacgg ccaggctggt gtcgaggtta acttccgtca    540
gcagaagcag aagttctcgg ctactcagct ggtcgccatg tacctgacca agatcagaga    600
tactgccgcc aacgaactgc aaatccccgt ctccgatgtc accatcagcg ttccgcctg    660 gttcaccgat gttcagcgcc gggcatgct tgacgctggt gagattgctg gtctcaaggt    720
tctgagactg atcaacgaca ccaccgccac cgctcttgga tatggtatca ctaagctcga    780
tctccccggt cccaggagaa agcctcgccg cgtcatgttc gttgatatcg ccacagcga    840 ctacaccgct tcgattgttg agttccgcaa gggtgaacta aacgtcaagg ctaccgcctg    900

-continued

```
cgaccgccac ttcggtggcc gtaacttcga ccttgccctc actgagcatt tcgccgagga   960
gttcaaggag aagttcaaga tcgacgttcg taagaacgcc aaggcttggg ctcgtaccct  1020
cgctgccgct gagaagatga agaaggtcct ttcggcgaac cctgctgccc ccatgagcat  1080
cgaatccctg atggaggacg tcgatgtccg cgccattgtc aagcgtgagg agctggagac  1140
catggttcag cctctcctgg agcgcgtcct tgttcccatc gagcaggccc tcgccgaggc  1200
caagctcaag cccgaggata ttgacagcat tgagatggtt ggtggctgca ctcgtgtccc  1260
ctccatcaag gaggccgttt ccaagttctt cggcaagaac ctttccttca ccctgaacca  1320
agatgaggcc atcgctcgcg ttgtgccttt cagctgtgcc atcctctccc ccgtcttccg  1380
tgtccgtgac ttctccgtgc acgacatcgt caactacccc atcgagttca cctgggagca  1440
gtccgcagat atccccgacg aggacaccag cctgaccgtc ttcggtcgcg gcaatgtcat  1500
gccctcgacc aagattctca cgttctaccg caagcagcct ttcgatctcg aagctcgtta  1560
cgctagcccc gaggagcttc ctggaaagac cgacccctgg gtgggccgct tctctgtcaa  1620
gggtgtcaag gccgatgcca acgatgactt catgatttgc aagctcaagg cccgcctgaa  1680
cttgcacggt atcctcaacg ttgagtctgg ttactacgtc gaggacatgg aagtggagga  1740
gcctgtcgag gaggatgctg atgtgagttg gattcgtatc gtaatgcgcg cagcttttgt  1800
tactaacatg cgactaggct atggacaccg atgctaaggg tgatgagcag cccaagaaga  1860
cccgcaaggt caagaagcag gttcgcaagg gcgacctgcc cattgtcgcc ggcacccctg  1920
ccattgagcc ttccgtcaag gaagcctgga tcgaaggcga aaggccatg tatctgcatg  1980
ataagactat cgccgagacc gacgagaaga gaacgagctc tgaaaccacg atttacgata  2040
tgcgtgacag gaaatatggt cgctacgcca gattcctcga agatgaggcg aagaagcagg  2100
ccttcgatga caagctggat gagctcgagg tatgttcact ctccttttct agccagatcg  2160
ccgtgtctgt caaggttttg tgctcgtgct aaccacgatt ttagaactgg ctgtatgatg  2220
atgagggcgg tgctgacacc actctcgatg tctatgctgg caagtccag gagatcaaga  2280
agctggtgca gccattcgag gagacccttg aggacgagcg ccagcaagct ctggctgaag  2340
agctcgctaa gaagcgcgct gaggaagaag ccaagcgcgc ggctgaagag caggccaaga  2400
aggccgcggc cgctgctatg aactttgaag agagaaatga gacgatgcct gatgctcctg  2460
ctcaggagga agcccccgct ggcgacaagc agtaa                              2495
```

<210> SEQ ID NO 4
<211> LENGTH: 713
<212> TYPE: PRT
<213> ORGANISM: Aspergillus oryzae

<400> SEQUENCE: 4

```
Met Ser Val Val Gly Ile Asp Phe Gly Ala Gln Ser Thr Lys Ile Gly
1               5                   10                  15

Val Ala Arg Asn Lys Gly Ile Asp Ile Ile Thr Asn Glu Val Ser Asn
            20                  25                  30

Arg Ser Thr Pro Ser Leu Ile Ser Phe Asp Asn Lys Cys Arg Tyr Leu
        35                  40                  45

Gly Glu Ala Ala Lys Thr Arg Glu Thr Ser Asn Leu Lys Asn Thr Val
    50                  55                  60

Ala Asn Leu Lys Arg Leu Ile Gly Arg Ser Phe Ser Asp Pro Asp Val
65                  70                  75                  80

Gln Ile Glu Gln Ser Phe Asn Thr Ala Thr Leu Cys Asp Val Asn Gly
                85                  90                  95
```

```
Gln Ala Gly Val Glu Val Asn Phe Arg Gln Lys Gln Lys Phe Ser
        100                 105                 110
Ala Thr Gln Leu Val Ala Met Tyr Leu Thr Lys Ile Arg Asp Thr Ala
            115                 120                 125
Ala Asn Glu Leu Gln Ile Pro Val Ser Asp Val Thr Ile Ser Val Pro
        130                 135                 140
Ala Trp Phe Thr Asp Val Gln Arg Arg Ala Met Leu Asp Ala Gly Glu
145                 150                 155                 160
Ile Ala Gly Leu Lys Val Leu Arg Leu Ile Asn Asp Thr Thr Ala Thr
                165                 170                 175
Ala Leu Gly Tyr Gly Ile Thr Lys Leu Asp Leu Pro Gly Pro Glu Glu
            180                 185                 190
Lys Pro Arg Arg Val Met Phe Val Asp Ile Gly His Ser Asp Tyr Thr
        195                 200                 205
Ala Ser Ile Val Glu Phe Arg Lys Gly Glu Leu Asn Val Lys Ala Thr
        210                 215                 220
Ala Cys Asp Arg His Phe Gly Gly Arg Asn Phe Asp Leu Ala Leu Thr
225                 230                 235                 240
Glu His Phe Ala Glu Glu Phe Lys Glu Lys Phe Lys Ile Asp Val Arg
                245                 250                 255
Lys Asn Ala Lys Ala Trp Ala Arg Thr Leu Ala Ala Ala Glu Lys Met
            260                 265                 270
Lys Lys Val Leu Ser Ala Asn Pro Ala Ala Pro Met Ser Ile Glu Ser
        275                 280                 285
Leu Met Glu Asp Val Asp Val Arg Ala Ile Val Lys Arg Glu Glu Leu
        290                 295                 300
Glu Thr Met Val Gln Pro Leu Leu Glu Arg Val Leu Val Pro Ile Glu
305                 310                 315                 320
Gln Ala Leu Ala Glu Ala Lys Leu Lys Pro Glu Asp Ile Asp Ser Ile
                325                 330                 335
Glu Met Val Gly Gly Cys Thr Arg Val Pro Ser Ile Lys Glu Ala Val
            340                 345                 350
Ser Lys Phe Phe Gly Lys Asn Leu Ser Phe Thr Leu Asn Gln Asp Glu
        355                 360                 365
Ala Ile Ala Arg Gly Cys Ala Phe Ser Cys Ala Ile Leu Ser Pro Val
        370                 375                 380
Phe Arg Val Arg Asp Phe Ser Val His Asp Ile Val Asn Tyr Pro Ile
385                 390                 395                 400
Glu Phe Thr Trp Glu Gln Ser Ala Asp Ile Pro Asp Glu Asp Thr Ser
                405                 410                 415
Leu Thr Val Phe Gly Arg Gly Asn Val Met Pro Ser Thr Lys Ile Leu
            420                 425                 430
Thr Phe Tyr Arg Lys Gln Pro Phe Asp Leu Glu Ala Arg Tyr Ala Ser
        435                 440                 445
Pro Glu Glu Leu Pro Gly Lys Thr Asp Pro Trp Val Gly Arg Phe Ser
        450                 455                 460
Val Lys Gly Val Lys Ala Asp Ala Asn Asp Asp Phe Met Ile Cys Lys
465                 470                 475                 480
Leu Lys Ala Arg Leu Asn Leu His Gly Ile Leu Asn Val Glu Ser Gly
                485                 490                 495
Tyr Tyr Val Glu Asp Met Glu Val Glu Glu Pro Val Glu Glu Asp Ala
            500                 505                 510
```

| | | | | | | | | | | | |
|---|---|---|---|---|---|---|---|---|---|---|---|
|Asp|Ala|Met|Asp|Thr|Asp|Ala|Lys|Gly|Asp|Glu|Gln|Pro|Lys|Lys|Thr|
| | |515| | | |520| | | |525| |

Arg Lys Val Lys Lys Gln Val Arg Lys Gly Asp Leu Pro Ile Val Ala
    530             535             540

Gly Thr Pro Ala Ile Glu Pro Ser Val Lys Glu Ala Trp Ile Glu Gly
545             550             555             560

Glu Lys Ala Met Tyr Leu His Asp Lys Thr Ile Ala Glu Thr Asp Glu
            565             570             575

Lys Lys Asn Glu Leu Glu Thr Thr Ile Tyr Asp Met Arg Asp Arg Lys
        580             585             590

Tyr Gly Arg Tyr Ala Arg Phe Leu Glu Asp Glu Ala Lys Lys Gln Ala
    595             600             605

Phe Asp Asp Lys Leu Asp Glu Leu Glu Asn Trp Leu Tyr Asp Asp Glu
    610             615             620

Gly Gly Ala Asp Thr Thr Leu Asp Val Tyr Ala Gly Lys Leu Gln Glu
625             630             635             640

Ile Lys Lys Leu Val Gln Pro Phe Glu Thr Leu Glu Asp Glu Arg
            645             650             655

Gln Gln Ala Leu Ala Glu Glu Leu Ala Lys Lys Arg Ala Glu Glu Glu
        660             665             670

Ala Lys Arg Ala Ala Glu Glu Gln Lys Lys Ala Ala Ala Ala Ala
    675             680             685

Met Asn Phe Glu Glu Arg Asn Glu Thr Met Pro Asp Ala Pro Ala Gln
    690             695             700

Glu Glu Ala Pro Ala Gly Asp Lys Gln
705             710

<210> SEQ ID NO 5
<211> LENGTH: 2173
<212> TYPE: DNA
<213> ORGANISM: Aspergillus oryzae

<400> SEQUENCE: 5

```
atgtccgaga cttttgagtt ccaggctgag atctctcagc tcctttctct tatcatcaac      60
actgtctact ccaacaagga gattttcctg cgtgaactta tctccaatgc ctccgatgcc     120
cttgacaaga tccgctatga gtctttgtcg gacccttcca agctcgactc aggcaaggac     180
ctccgtatcg atatcattcc caacaaggag gccaagacct tgactatccg tgataccggt     240
atcggtatga ccaaggctgt aagtcaatct cgtctcggtt gccattatat gtctacacag     300
accccaatct aatcatatcg cttttgtata ggacctgatc aacaaccttg gtaccatcgc     360
tcgctctggt accaagcagt tcatggaagc cctctccgca ggtgccgata tttccatgat     420
tggccagttc ggtgttggct ctactctgc ttaccttgtc gctgaccgcg tcactgtcat     480
ctctaagcac aacgatgatg agcagtacgt ctgggagtcc gctgccggcg gtaccttcac     540
gctcacccag gacaccgagg gtgagcccct tggccgtggt accagatga tccttcactt     600
gaaggatgag cagaccgact acctcaacga gagccgcatc aaggaggttg ttcgcaagca     660
ctccgaattc atctcttacc ccatctacct ccacgttctg aaggaaaccg agaaggaggt     720
tcctgatgag gaggaagaga ccaaggaaga ggaaggcgat gagaaaaagc ccaaaattga     780
ggaggttgac gaagaagaag aaaagaagga gaagaagacc aagactgtca aggagagcaa     840
gatcgaggag gaggagctca acaagactaa gcccatctgg acccgtaacc ctgctgatat     900
cactcaggag gaatacgctg ccttctacaa gtctctctcc aatgactggg aggatcacct     960
```

```
tgccgtcaag cacttctccg ttgagggtca gctcgagttc cgtgccatcc tctatattcc   1020
taagcgtgct cctttcgacc tcttcgagac caagaagact aagaacaaca tcaagctcta   1080
tgttcgccgt gtcttcatca ccgacgacgc caccgacctc atccctgagt ggctcagctt   1140
catcaagggt gttgttgatt cagaggacct tcctctcaac ttgtcccgtg agaccctgca   1200
gcagaacaag atcatgaagg ttatcaaaaa gaacattgtc aagaagaccc ttgagctctt   1260
caccgagatt gctgaagacc gtgagcagtt tgacaagttc tactccgcct tcagcaagaa   1320
catcaaactt ggtgtccacg aggatgctca gaaccgccag actctcgcta agctgctccg   1380
ttaccagtcc accaagtcgg gtgatgaggt cacctccctc tctgactatg tcacccgcat   1440
gcctgagcac cagaagcaaa tctactacat cactggcgag tctatcaagg ctgtcgccaa   1500 gtctccttc cttgacagcc tcaagcgaaa gaactttgag gttctcttcc tggttgaccc   1560
tattgatgag tacgctttca ctcagcttaa ggagtttgat ggcaagaagc ttgtcgacat   1620
cactaaggac ttcgaactcg aggagtccga ggaggagaag gctgagcgtg agaaggagga   1680
gaaggagttc gagggcctcg ccaagagcct taagaacatc ctcggtgaca aggttgagaa   1740
ggttgttgtc tctcacaaac ttgttggctc tccttgcgcc atccgtactg ccagtttgg   1800 ttggtctgcc aatatggagc gtatcatgaa ggcccaggcc ctccgtgaca cctccatgag   1860
ctcctacatg tcttccaaga gaccttcga gatctctccc aagtctgcta tcatcaagga   1920
gctcaagaag aaggtcgagg ctgatggtga agcgaccgt accgtcaagt ccatcactca   1980
gcttctgttc gagacctctc ttttggtttc cggcttcacc atcgacgagc ctgccagctt   2040
tgccgagcgc atccacaagc ttgtgtctct tggtctgaac gtcgacgagg aggctgagac   2100
ctctgaggaa aaggccgctg aggaggctcc tgccgctgcc accggtgaga gctccatgga   2160
ggaggttgac taa                                                      2173
```

<210> SEQ ID NO 6
<211> LENGTH: 699
<212> TYPE: PRT
<213> ORGANISM: Aspergillus oryzae

<400> SEQUENCE: 6

Met Ser Glu Thr Phe Glu Phe Gln Ala Glu Ile Ser Gln Leu Leu Ser
1               5                   10                  15

Leu Ile Ile Asn Thr Val Tyr Ser Asn Lys Glu Ile Phe Leu Arg Glu
            20                  25                  30

Leu Ile Ser Asn Ala Ser Asp Ala Leu Asp Lys Ile Arg Tyr Glu Ser
        35                  40                  45

Leu Ser Asp Pro Ser Lys Leu Asp Ser Gly Lys Asp Leu Arg Ile Asp
    50                  55                  60

Ile Ile Pro Asn Lys Glu Ala Lys Thr Leu Thr Ile Arg Asp Thr Gly
65                  70                  75                  80

Ile Gly Met Thr Lys Ala Asp Leu Ile Asn Asn Leu Gly Thr Ile Ala
                85                  90                  95

Arg Ser Gly Thr Lys Gln Phe Met Glu Ala Leu Ser Ala Gly Ala Asp
            100                 105                 110

Ile Ser Met Ile Gly Gln Phe Gly Val Gly Phe Tyr Ser Ala Tyr Leu
        115                 120                 125

Val Ala Asp Arg Val Thr Val Ile Ser Lys His Asn Asp Asp Glu Gln
    130                 135                 140

Tyr Val Trp Glu Ser Ala Ala Gly Gly Thr Phe Thr Leu Thr Gln Asp
145                 150                 155                 160

```
Thr Glu Gly Glu Pro Leu Gly Arg Gly Thr Lys Met Ile Leu His Leu
            165                 170                 175
Lys Asp Glu Gln Thr Asp Tyr Leu Asn Glu Ser Arg Ile Lys Glu Val
            180                 185                 190
Val Arg Lys His Ser Glu Phe Ile Ser Tyr Pro Ile Tyr Leu His Val
            195                 200                 205
Leu Lys Glu Thr Glu Lys Glu Val Pro Asp Glu Glu Glu Glu Thr Lys
            210                 215                 220
Glu Glu Glu Gly Asp Glu Lys Lys Pro Lys Ile Glu Glu Val Asp Glu
225                 230                 235                 240
Glu Glu Glu Lys Lys Glu Lys Lys Thr Lys Thr Val Lys Glu Ser Lys
            245                 250                 255
Ile Glu Glu Glu Glu Leu Asn Lys Thr Lys Pro Ile Trp Thr Arg Asn
            260                 265                 270
Pro Ala Asp Ile Thr Gln Glu Glu Tyr Ala Ala Phe Tyr Lys Ser Leu
            275                 280                 285
Ser Asn Asp Trp Glu Asp His Leu Ala Val Lys His Phe Ser Val Glu
            290                 295                 300
Gly Gln Leu Glu Phe Arg Ala Ile Leu Tyr Ile Pro Lys Arg Ala Pro
305                 310                 315                 320
Phe Asp Leu Phe Glu Thr Lys Lys Thr Lys Asn Asn Ile Lys Leu Tyr
            325                 330                 335
Val Arg Arg Val Phe Ile Thr Asp Asp Ala Thr Asp Leu Ile Pro Glu
            340                 345                 350
Trp Leu Ser Phe Ile Lys Gly Val Val Asp Ser Glu Asp Leu Pro Leu
            355                 360                 365
Asn Leu Ser Arg Glu Thr Leu Gln Gln Asn Lys Ile Met Lys Val Ile
            370                 375                 380
Lys Lys Asn Ile Val Lys Lys Thr Leu Glu Leu Phe Thr Glu Ile Ala
385                 390                 395                 400
Glu Asp Arg Glu Gln Phe Asp Lys Phe Tyr Ser Ala Phe Ser Lys Asn
            405                 410                 415
Ile Lys Leu Gly Val His Glu Asp Ala Gln Asn Arg Gln Thr Leu Ala
            420                 425                 430
Lys Leu Leu Arg Tyr Gln Ser Thr Lys Ser Gly Asp Glu Val Thr Ser
            435                 440                 445
Leu Ser Asp Tyr Val Thr Arg Met Pro Glu His Gln Lys Gln Ile Tyr
            450                 455                 460
Tyr Ile Thr Gly Glu Ser Ile Lys Ala Val Ala Lys Ser Pro Phe Leu
465                 470                 475                 480
Asp Ser Leu Lys Gln Lys Asn Phe Glu Val Leu Phe Leu Val Asp Pro
            485                 490                 495
Ile Asp Glu Tyr Ala Phe Thr Gln Leu Lys Glu Phe Asp Gly Lys Lys
            500                 505                 510
Leu Val Asp Ile Thr Lys Asp Phe Glu Leu Glu Glu Ser Glu Glu Glu
            515                 520                 525
Lys Ala Glu Arg Glu Lys Glu Glu Lys Glu Phe Glu Gly Leu Ala Lys
            530                 535                 540
Ser Leu Lys Asn Ile Leu Gly Asp Lys Val Glu Lys Val Val Val Ser
545                 550                 555                 560
His Lys Leu Val Gly Ser Pro Cys Ala Ile Arg Thr Gly Gln Phe Gly
            565                 570                 575
```

```
Trp Ser Ala Asn Met Glu Arg Ile Met Lys Ala Gln Ala Leu Arg Asp
            580                 585                 590

Thr Ser Met Ser Ser Tyr Met Ser Lys Lys Thr Phe Glu Ile Ser
        595                 600                 605

Pro Lys Ser Ala Ile Ile Lys Glu Leu Lys Lys Val Glu Ala Asp
            610                 615                 620

Gly Glu Ser Asp Arg Thr Val Lys Ser Ile Thr Gln Leu Leu Phe Glu
625                 630                 635                 640

Thr Ser Leu Leu Val Ser Gly Phe Thr Ile Asp Glu Pro Ala Ser Phe
                645                 650                 655

Ala Glu Arg Ile His Lys Leu Val Ser Leu Gly Leu Asn Val Asp Glu
            660                 665                 670

Glu Ala Glu Thr Ser Glu Glu Lys Ala Ala Glu Glu Ala Pro Ala Ala
            675                 680                 685

Ala Thr Gly Glu Ser Ser Met Glu Glu Val Asp
            690                 695
```

<210> SEQ ID NO 7
<211> LENGTH: 34
<212> TYPE: DNA
<213> ORGANISM: Artificial Sequence
<220> FEATURE:
<223> OTHER INFORMATION: Primer oAT3702

<400> SEQUENCE: 7
ccattgtgcc tgtggggttt attgttcaga gaag                              34

<210> SEQ ID NO 8
<211> LENGTH: 22
<212> TYPE: DNA
<213> ORGANISM: Artificial Sequence
<220> FEATURE:
<223> OTHER INFORMATION: Primer oAT3703

<400> SEQUENCE: 8
ccacaggcac aatggccccc gc                                           22

<210> SEQ ID NO 9
<211> LENGTH: 36
<212> TYPE: DNA
<213> ORGANISM: Artificial Sequence
<220> FEATURE:
<223> OTHER INFORMATION: Primer oAT3704

<400> SEQUENCE: 9
tgtcagtgtg aaccgacgta gcctgttttg aattcc                            36

<210> SEQ ID NO 10
<211> LENGTH: 30
<212> TYPE: DNA
<213> ORGANISM: Artificial Sequence
<220> FEATURE:
<223> OTHER INFORMATION: Primer oAT3705

<400> SEQUENCE: 10
cggttcacac tgacagagga tggagttctg                                   30

<210> SEQ ID NO 11
<211> LENGTH: 32
<212> TYPE: DNA
<213> ORGANISM: Artificial Sequence
<220> FEATURE:
<223> OTHER INFORMATION: Primer oAT3706

```
<400> SEQUENCE: 11
cccacaggca tcatgtccga gacttttgag tt                                32

<210> SEQ ID NO 12
<211> LENGTH: 52
<212> TYPE: DNA
<213> ORGANISM: Artificial Sequence
<220> FEATURE:
<223> OTHER INFORMATION: Primer oAT3707

<400> SEQUENCE: 12
cgatcatcga gaattccatg gtgttttgat cattttaaat ttttatatgg cg          52

<210> SEQ ID NO 13
<211> LENGTH: 33
<212> TYPE: DNA
<213> ORGANISM: Artificial Sequence
<220> FEATURE:
<223> OTHER INFORMATION: Primer oAT3708

<400> SEQUENCE: 13
catgatgcct gtggggttta ttgttcagag aag                               33

<210> SEQ ID NO 14
<211> LENGTH: 53
<212> TYPE: DNA
<213> ORGANISM: Artificial Sequence
<220> FEATURE:
<223> OTHER INFORMATION: Primer oAT3709

<400> SEQUENCE: 14
ccgcggccgc gaattccatg gtgttttgat cattttaaat ttttatatgg cgg         53

<210> SEQ ID NO 15
<211> LENGTH: 38
<212> TYPE: DNA
<213> ORGANISM: Artificial Sequence
<220> FEATURE:
<223> OTHER INFORMATION: Primer oAT3713

<400> SEQUENCE: 15
tgagagtgca ccatagatct gtaggagtga gtacccgg                          38

<210> SEQ ID NO 16
<211> LENGTH: 36
<212> TYPE: DNA
<213> ORGANISM: Artificial Sequence
<220> FEATURE:
<223> OTHER INFORMATION: Primer oAT3714

<400> SEQUENCE: 16
gccattgtgg ctctgtttag atgtgtctat gtggcg                            36

<210> SEQ ID NO 17
<211> LENGTH: 23
<212> TYPE: DNA
<213> ORGANISM: Artificial Sequence
<220> FEATURE:
<223> OTHER INFORMATION: Primer oAT3715

<400> SEQUENCE: 17
acagagccac aatggccccc gct                                          23

<210> SEQ ID NO 18
```

<210> SEQ ID NO 18
<211> LENGTH: 32
<212> TYPE: DNA
<213> ORGANISM: Artificial Sequence
<220> FEATURE:
<223> OTHER INFORMATION: Primer oAT3716

<400> SEQUENCE: 18
aacagagcat gtccgagact tttgagttcc ag                          32

<210> SEQ ID NO 19
<211> LENGTH: 35
<212> TYPE: DNA
<213> ORGANISM: Artificial Sequence
<220> FEATURE:
<223> OTHER INFORMATION: Primer oAT3717

<400> SEQUENCE: 19
ctcggacatg ctctgtttag atgtgtctat gtggc                       35

<210> SEQ ID NO 20
<211> LENGTH: 38
<212> TYPE: DNA
<213> ORGANISM: Artificial Sequence
<220> FEATURE:
<223> OTHER INFORMATION: Primer oAT3718

<400> SEQUENCE: 20
cgatcatcga gaattgatct gtaggagtga gtacccgg                    38

<210> SEQ ID NO 21
<211> LENGTH: 30
<212> TYPE: DNA
<213> ORGANISM: Artificial Sequence
<220> FEATURE:
<223> OTHER INFORMATION: Primer oAT3719

<400> SEQUENCE: 21
cggttcacac tgacacaact gaatgcgccc                             30

<210> SEQ ID NO 22
<211> LENGTH: 32
<212> TYPE: DNA
<213> ORGANISM: Artificial Sequence
<220> FEATURE:
<223> OTHER INFORMATION: Primer oAT3720

<400> SEQUENCE: 22
cccacaggca tcatgagtgt agttggaatc ga                          32

<210> SEQ ID NO 23
<211> LENGTH: 52
<212> TYPE: DNA
<213> ORGANISM: Artificial Sequence
<220> FEATURE:
<223> OTHER INFORMATION: Primer oAT3725

<400> SEQUENCE: 23
tcactcctac agatccatgg tgttttgatc attttaaatt tttatatggc gg    52

<210> SEQ ID NO 24
<211> LENGTH: 38
<212> TYPE: DNA
<213> ORGANISM: Artificial Sequence
<220> FEATURE:
<223> OTHER INFORMATION: Primer oAT3726

<400> SEQUENCE: 24

```
gatcaaaaca ccatggatct gtaggagtga gtacccgg                                    38

<210> SEQ ID NO 25
<211> LENGTH: 30
<212> TYPE: DNA
<213> ORGANISM: Artificial Sequence
<220> FEATURE:
<223> OTHER INFORMATION: Primer oAT3727

<400> SEQUENCE: 25
gatcatcgag aattcgagga tggagttctg                                             30
```

FUNGAL CHAPERONE PROTEINS

CROSS-REFERENCE TO RELATED APPLICATIONS

This application is a 35 U.S.C. 371 national application of PCT/EP2019/057416, filed Mar. 25, 2019, which claims priority or the benefit under 35 U.S.C. 119 of European application no. 18163921.2, filed Mar. 26, 2018. The contents of these applications are fully incorporated herein by reference.

REFERENCE TO SEQUENCE LISTING

This application contains a Sequence Listing in computer readable form that was submitted as an ASCII text file named 14720-WO-PCT seq.list 25-MAR-2019.txt (created on Mar. 25, 2019, containing 29 kb), which is incorporated herein by reference.

FIELD OF THE INVENTION

The present invention relates to fungal host cells comprising nucleic acid constructs comprising a heterologous promoter operably linked to polynucleotidea encoding a chaperone, nucleic acid constructs comprising a polynucleotide encoding a chaperone, and methods for producing polypeptides of interest.

BACKGROUND OF THE INVENTION

Within industrial biotechnology, there is a continuous need for improving production yield and thereby process profitability in the production of enzymes and other industrially relevant proteins. A successful strategy thus far has been to employ production host cells that over-express the gene encoding the target protein. There are known and readily available methods for doing this, such as increasing gene expression by using multicopy plasmids or enhancing the activity of the gene by modifying its control sequences, e.g., by using strong promoters, or multiple promoters. Dramatic improvements in the synthesis of secreted proteins have been achieved this way, up to a level at which additional improvements of gene expression are of no further benefit because of bottlenecks in the secretion machinery. Thus, methods of increasing the secretory capacity of production host cells are highly warranted, since such improvements would work in parallel with the well-known concept of gene over-expression and result in additive or even synergistic effects on the overall production yield.

Chaperones are proteins that assist in folding of other proteins. Over-expression of one or more chaperones in a production host cell may provide an enhanced folding of a given target protein, which in turn is likely to result in enhanced secretion of correctly folded protein and thereby an improved production yield. Chaperone over-expression has been used for optimization of prokaryotic host cells (see, e.g., WO 1994/019471; Westers et al. *Bacillus subtilis* as cell factory for pharmaceutical proteins: a biotechnological approach to optimize the host organism *Biochem. Biophys. Acta.*, vol. 1694, pp. 299-310, 2004). Various chaperones have also been described in fungal organisms with emphasis on yeast (see, e.g., Verghese et al. Biology of the Heat Shock Response and Protein Chaperones: Budding Yeast (*Saccharomyces cerevisiae*) as a Model System. *Microbiol. Mol. Biol. Rev.*, vol. 76, pp. 115-158, 2012), and to a lesser extent in filamentous fungi (see, e.g., Conesa et al. The secretion pathway in filamentous fungi: a biotechnological view. *Fungal Genetics and Biology*, vol. 33, pp. 155-171, 2001).

In fungal host cells, the majority of the extracellular proteins are secreted via the conventional protein secretion (CPS) pathway, which involves vesicle-mediated transport from the endoplasmic reticulum (ER) through the Golgi apparatus to the cell membrane. However, studies have also reported extracellular proteins secreted independently of the classical ER-Golgi pathway. This process is known as the unconventional protein secretion (UPS) pathway and includes several distinct vesicular and non-vesicular transport pathways. The UPS pathway has not yet been fully elucidated, but evidence of protein secreted via the UPS pathway has recently been described in filamentous fungi (see, e.g., Burgraaf et al. The unconventional secretion of PepN is independent of a functional autophagy machinery in the filamentous fungus *A. niger. FEMS Microbiology Lett.*, vol. 363, pp. 1-7, 2016; Kwon et al. Analysis of an acyl-CoA biding protein in *A. oryzae* that undergoes unconventional secretion. *Biochem. Biophys. Res. Com.*, vol. 493, pp. 481-486, 2017).

Depending on the target protein, it may be beneficial to harness either one or both of these pathways in order to optimize protein secretion in fungal host cells. Thus, due to the continuous need in the art for improving production yield, identification of further chaperones capable of aiding protein secretion via the CPS pathway and/or the UPS pathway is highly warranted.

SUMMARY OF THE INVENTION

The invention provides means and methods for utilizing the fungal chaperones Ssa2, Sse2, and Hsc82 for improving production of industrially relevant polypeptides.

In a first aspect, the present invention relates to a fungal host cell comprising in its genome at least one polynucleotide encoding a polypeptide of interest; and at least one nucleic acid construct selected from the group consisting of:
  a) a nucleic acid construct comprising a heterologous promoter operably linked to a polynucleotide encoding an Ssa2 protein;
  b) a nucleic acid construct comprising a heterologous promoter operably linked to a polynucleotide encoding an Sse2 protein;
  c) a nucleic acid construct comprising a heterologous promoter operably linked to a polynucleotide encoding an Hsc82 protein; and
  d) any combination of (a), (b), and (c).

In a second aspect, the present invention relates to a nucleic acid construct comprising:
  a) a heterologous promoter operably linked to a polynucleotide encoding an Ssa2 protein; OR
  b) a heterologous promoter operably linked to a polynucleotide encoding an Sse2 protein; OR
  c) a heterologus promoter operably linked to a polynucleotide encoding an Hsc82 protein.

In a third aspect, the present invention relates to a method for producing a polypeptide of interest, the method comprising:
  a) providing a fungal host cell of the first aspect;
  b) cultivating said host cell under conditions conducive for expression of the polypeptide of interest; and, optionally
  c) recovering the polypeptide of interest.

Figure 1:
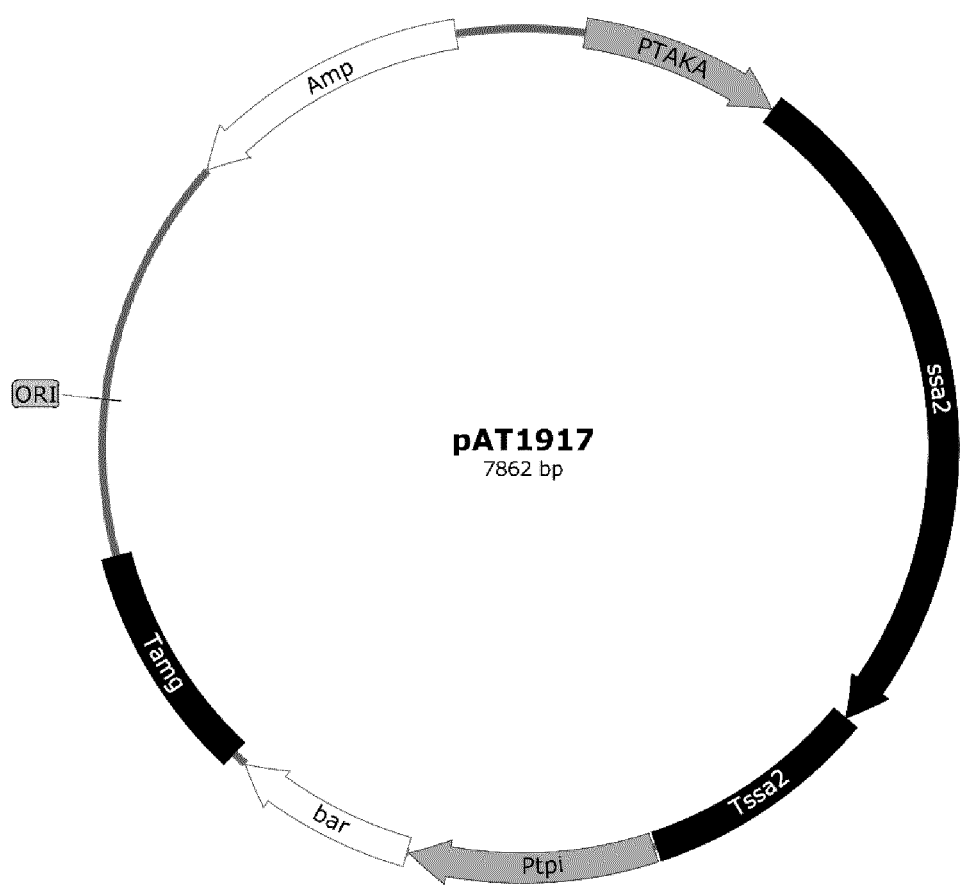
FIG. 1 shows plasmid pAT1917 for over-expression of the ssa2 gene in *A. oryzae*.

DEFINITIONS cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fungal host cell: The term "fungal host cell" means any fungal cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature.

Heterologous promoter: The term "heterologous promoter" means a promoter that is foreign (i.e., from a different gene) to the polynucleotide to which it is operably linked.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Variant: The term "variant" means a polypeptide comprising an alteration, i.e., a substitution, insertion, and/or deletion, at one or more (e.g., several) positions compared to the corresponding native polypeptide. A substitution means replacement of the amino acid occupying a position with a different amino acid; a deletion means removal of the amino acid occupying a position; and an insertion means adding an amino acid adjacent to and immediately following the amino acid occupying a position.

SEQUENCE LISTING

| SEQ ID NO | Name |
|---|---|
| 1 | DNA sequence encoding Ssa2 from *A. oryzae* |
| 2 | Amino acid sequence of Ssa2 from *A. oryzae* |
| 3 | DNA sequence encoding Sse2 from *A. oryzae* |
| 4 | Amino acid sequence of Sse2 from *A. oryzae* |
| 5 | DNA sequence encoding Hsc82 from *A. oryzae* |
| 6 | Amino acid sequence of Hsc82 from *A. oryzae* |
| 7 | Primer oAT3702 |
| 8 | Primer oAT3703 |
| 9 | Primer oAT3704 |
| 10 | Primer oAT3705 |
| 11 | Primer oAT3706 |
| 12 | Primer oAT3707 |
| 13 | Primer oAT3708 |
| 14 | Primer oAT3709 |
| 15 | Primer oAT3713 |
| 16 | Primer oAT3714 |
| 17 | Primer oAT3715 |
| 18 | Primer oAT3716 |
| 19 | Primer oAT3717 |
| 20 | Primer oAT3718 |
| 21 | Primer oAT3719 |
| 22 | Primer oAT3720 |
| 23 | Primer oAT3725 |
| 24 | Primer oAT3726 |
| 25 | Primer oAT3727 |

DETAILED DESCRIPTION OF THE INVENTION

Using a proteomics approach, three chaperones, Ssa2, Sse2, and Hsc82, have been identified as being involved in the protein secretion pathways of the filamentous fungus *Aspergillus oryzae*. The expression pattern of Ssa2 correlates with the expression and secretion profile of lipoxygenase, and the expression patterns of both Ssa2 as well as Hsc82 correlate with the expression and secretion profile of haloperoxidase. Moreover, over-expression of Ssa2, Sse2, and/or Hsc82, either alone or in combination, results in increased amounts of secreted enzyme and/or increased enzyme activity. This surprising finding clearly indicate that Ssa2, Sse2, and Hsc82 are useful chaperones with respect to improving production of industrially relevant polypeptides such as enzymes.

Fungal Host Cells

In a first aspect, the present invention relates to a fungal host cell comprising in its genome at least one polynucleotide encoding a polypeptide of interest; and at least one nucleic acid construct selected from the group consisting of:

a) a nucleic acid construct comprising a heterologous promoter operably linked to a polynucleotide encoding an Ssa2 protein;

b) a nucleic acid construct comprising a heterologous promoter operably linked to a polynucleotide encoding an Sse2 protein;

c) a nucleic acid construct comprising a heterologous promoter operably linked to a polynucleotide encoding an Hsc82 protein; and
d) any combination of (a), (b), and (c).

In a preferred embodiment, the fungal host cells of the invention comprise at least one polynucleotide encoding a polypeptide of interest; and
   i) at least one nucleic acid construct comprising a heterologous promoter operably linked to a polynucleotide encoding an Ssa2 protein AND at least one nucleic acid construct comprising a heterologous promoter operably linked to a polynucleotide encoding an Sse2 protein; OR
   ii) at least one nucleic acid construct comprising a heterologous promoter operably linked to a polynucleotide encoding an Ssa2 protein AND at least one nucleic acid construct comprising a heterologous promoter operably linked to a polynucleotide encoding an Hsc82 protein; OR
   iii) at least one nucleic acid construct comprising a heterologous promoter operably linked to a polynucleotide encoding an Sse2 protein AND at least one nucleic acid construct comprising a heterologous promoter operably linked to a polynucleotide encoding an Hsc82 protein; OR
   iv) at least one nucleic acid construct comprising a heterologous promoter operably linked to a polynucleotide encoding an Ssa2 protein AND at least one nucleic acid construct comprising a heterologous promoter operably linked to a polynucleotide encoding an Sse2 protein AND at least one nucleic acid construct comprising a heterologous promoter operably linked to a polynucleotide encoding an Hsc82 protein.

The fungal host cell comprises at least one, e.g., at least two, at least three, at least four, at least five, at least six, at least seven, at least eight, at least nine, at least ten, or more, polynucleotides encoding a polypeptide of interest.

The polypeptide of interest may be any polypeptide. In an embodiment, the polypeptide of interest is a heterologous polypeptide. Preferably, the polypeptide of interest comprises an enzyme, preferably a hydrolase, isomerase, ligase, lyase, oxidoreductase, or transferase; more preferably an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, nuclease, oxidase, pectinolytic enzyme, peroxidase, phosphodiesterase, phytase, polyphenoloxidase, proteolytic enzyme, ribonuclease, transglutaminase, xylanase, or beta-xylosidase. Preferably, the polypeptide of interest is secreted; more preferably the polypeptide of interest is secreted via the CPS pathway and/or the UPS pathway; most preferably the polypeptide of interest is secreted via the UPS pathway.

In a preferred embodiment, the fungal host cell further comprises one or more, e.g., at least two, at least three, at least four, at least five, at least six, at least seven, at least eight, at least nine, at least ten, or more, additional polynucleotides encoding one or more, e.g., at least two, at least three, at least four, at least five, at least six, at least seven, at least eight, at least nine, at least ten, or more, additional polypeptides of interest. The one or more additional polypeptide of interest may be heterologous polypeptides. Preferably, the one or more additional polypeptides of interest comprise an enzyme, preferably a hydrolase, isomerase, ligase, lyase, oxidoreductase, or transferase; more preferably an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, nuclease, oxidase, pectinolytic enzyme, peroxidase, phosphodiesterase, phytase, polyphenoloxidase, proteolytic enzyme, ribonuclease, transglutaminase, xylanase, or beta-xylosidase. Preferably, the one or more additional polypeptides of interest are secreted; more preferably the one or more additional polypeptides of interest are secreted via the CPS pathway and/or the UPS pathway; most preferably the one or more additional polypeptides of interest are secreted via the UPS pathway.

The fungal host cell may comprise at least one, e.g., at least two, at least three, at least four, at least five, at least six, at least seven, at least eight, at least nine, at least ten, or more, nucleic acid constructs comprising a heterologous promoter operably linked to a polynucleotide encoding an Ssa2 protein The Ssa2 protein may be any Ssa2 protein, including fragments, homologues, and variants thereof. Preferably, the Ssa2 protein has at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:2.

The Ssa2 protein is expressed from a nucleic acid construct comprising a heterologous promoter operably linked to a polynucleotide encoding the Ssa2 protein. Preferably, the polynucleotide encoding the Ssa2 protein has at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:1.

The fungal host cell may also comprise at least one, e.g., at least two, at least three, at least four, at least five, at least six, at least seven, at least eight, at least nine, at least ten, or more, nucleic acid constructs comprising a heterologous promoter operably linked to a polynucleotide encoding an Sse2 protein The Sse2 protein may be any Sse2 protein, including fragments, homologues, and variants thereof. Preferably, the Sse2 protein has at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:4.

The Sse2 protein is expressed from a nucleic acid construct comprising a heterologous promoter operably linked to a polynucleotide encoding the Sse2 protein. Preferably, the polynucleotide encoding the Sse2 protein has at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:3.

The fungal host may also comprise at least one, e.g., at least two, at least three, at least four, at least five, at least six, at least seven, at least eight, at least nine, at least ten, or more, nucleic acid constructs comprising a heterologous promoter operably linked to a polynucleotide encoding an Hsc82 protein. The Hsc82 protein may be any Hsc82 protein, including fragments, homologues and variants thereof. Preferably, the Hsc82 protein has at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:6.

The Hsc82 protein is expressed from a nucleic acid construct comprising a heterologous promoter operably linked to a polynucleotide encoding the Hsc82 protein. Preferably the polynucleotide encoding the Hsc82 protein has at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:5.

The heterologous promoter operably linked to the Ssa2 protein, the Sse2 protein, and/or the Hsc82 protein may be either same or different. Preferably, the heterologous promoter(s) are, independently, selected from the group consisting of PamyB, Pgpd, Ptef1, PacuN, and PTAKA.

In a preferred embodiment, the heterologous promoter is PamyB.

In a preferred embodiment, the heterologous promoter is PTAKA.

In a preferred embodiment, the heterologous promoter is Pgpd.

The choice of fungal host cell will to a large extent depend upon the gene encoding the polypeptide of interest and its source. The term "host cell" encompasses any progeny of a parent cell that is not identical to the parent cell due to mutations that occur during replication A nucleic acid construct of the invention or a vector comprising a nucleic acid construct of the invention may be introduced into the fungal host cell so that the construct or vector is maintained as a chromosomal integrant or as a self-replicating extra-chromosomal vector as described below.

The host cell may be any fungal cell. "Fungi" as used herein includes the phyla Ascomycota, Basidiomycota, Chytridiomycota, and Zygomycota as well as the Oomycota and all mitosporic fungi (as defined by Hawksworth et al., In, Ainsworth and Bisby's Dictionary of The Fungi, 8th edition, 1995, CAB International, University Press, Cambridge, UK).

The fungal host cell may be a yeast cell. "Yeast" as used herein includes ascosporogenous yeast (*Endomycetales*), basidiosporogenous yeast, and yeast belonging to the *Fungi Imperfecti* (*Blastomycetes*). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarchroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Polynucleotides

The present invention also relates to polynucleotides encoding a polypeptide of interest, polynucleotides encoding an Ssa2 protein, polynucleotides encoding an Sse2 protein, and polynucleotides encoding an Hsc82 protein. In an embodiment, the polynucleotides of the invention have been isolated.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used.

The polynucleotides encoding an Ssa2 protein, an Sse2 protein, and an Hsc82 protein may be cloned from a strain of *Aspergilus*, or a related organism and thus, for example, may be an allelic or species variant of the polypeptide encoding region of the polynucleotides.

Modification of a polynucleotide encoding a polypeptide of interest, an Ssa2 protein, and Sse2 protein, and/or an HSc82 protein may be necessary for synthesizing polypeptides substantially similar to said polypeptide, said Ssa2 protein, said Sse2 protein, and/or said Hsc82 proteins The term "substantially similar" to the polypeptide, the Ssa2 protein, the Sse2 protein, and/or the Hsc82 protein refers to non-naturally occurring forms of the polypeptide and/or proteins.

Nucleic Acid Constructs

In a second aspect, the present invention relates to a nucleic acid construct comprising:
 a) a heterologous promoter operably linked to a polynucleotide encoding an Ssa2 protein; OR
 b) a heterologous promoter operably linked to a polynucleotide encoding an Sse2 protein; OR
 c) a heterologous promoter operably linked to a polynucleotide encoding an Hsc82 protein.

In a preferred embodiment, the heterologous promoter is selected from the group consisting of PamyB, Pgpd, Ptef1, PacuN, and PTAKA; preferably, the heterologous promoter is PamyB, Pgpd, or PTAKA.

The Ssa2 protein expressed from the nucleic acid construct may be any Ssa2 protein, including fragments, homologoues, and variants thereof. Preferably, the Ssa2 protein has at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:2.

Preferably, the polynucleotide encoding the Ssa2 protein has at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:1.

The Sse2 protein expressed from the nucleic acid construct may be any Sse2 protein, including fragments, homologoues, and variants thereof. Preferably, the Sse2 protein has at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:4.

Preferably, the polynucleotide encoding the Sse2 protein has at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:3.

The Hsc82 protein expressed from the nucleic acid construct may be any Hsc82 protein, including fragments, homologoues and variants thereof. Preferably, the Hsc82 protein has at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:6.

Preferably, the polynucleotide encoding the Hsc82 protein has at least 70%, e.g., at least 75%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO:5.

In addition to a heterologous promoter, the nucleic acid constructs of the invention may comprise additional control sequences that direct the expression of the polynucleotide encoding an Ssa2 protein, an Sse2 protein, or an Hsc82 protein in a suitable fungal host cell under conditions compatible with the control sequences.

The polynucleotide may be manipulated in a variety of ways to provide for expression of the Ssa2 protein, Sse2 protein, or Hsc82 protein. Manipulation of the polynucleotide prior to its insertion into a vector may be desirable or necessary depending on the expression vector. The techniques for modifying polynucleotides utilizing recombinant DNA methods are well known in the art.

The nucleic acid constructs of the invention comprises a heterologous promoter. A promoter is a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell. A heterologous promoter is preferred for expression of Ssa2 protein, Sse2 protein, and Hsc82 protein. The heterologous promoter may either be the same or different, depending on the need to regulate expression simultaneously or independently.

Examples of suitable promoters for directing transcription of the nucleic acid constructs encoding an Ssa2 protein, an Sse2 protein, and/or and Hsc82 protein in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof. Other promoters are described in U.S. Pat. No. 6,011,147.

Preferably, the heterologous promoter is selected from the group consisting of PamyB, Pgpd, Ptef1, PacuN, and PTAKA.

In a preferred embodiment, the promoter is PamyB.
In a preferred embodiment, the promoter is PTAKA.
In a preferred embodiment, the promoter is Pgpd.

In a yeast host cell, useful promoters are obtained from the genes for *Saccharomyces cerevisiae* enolase (ENO 1), *Saccharomyces cerevisiae* galactokinase (GAL1), *Saccharomyces cerevisiae* alcohol dehydrogenase/glyceraldehyde-3 phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3 phosphoglycerate kinase. Other useful promoters for yeast host cells are described by Romanos et al., 1992, Yeast 8: 423-488.

The nucleic acid constructs of the invention may also comprise a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusariurn oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The nucleic acid constructs of the invention may also comprise a leader, a nontranslated region of an mRNA that is important for translation by the host cell, such as a 5' untranslated transcribed region (5' UTR). This 5' UTR or similar sequence is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase, *Aspergillus nidulans* triose phosphate isomerase, and *Aspergillus niger* aryl sulfatase (payA).

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The nucleic acid constructs of the invention may also comprise a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The nucleic acid constructs of the invention may also comprise a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The nucleic acid constructs of the invention may also comprise a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo. Examples of origins of replication for use in a yeast host cell are the 2 micron origin of replication, ARS1, ARS4, the combination of ARS1 and CEN3, and the combination of ARS4 and CEN6. Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Methods of Production

In a third aspect, the present invention also relates to methods of producing a polypeptide of interest, the method comprising:
 I) providing a fungal host cell comprising in its genome at least one polynucleotide encoding said polypeptide of interest; and at least one nucleic acid construct selected from the group consisting of:
  a) a nucleic acid construct comprising a heterologous promoter operably linked to polynucleotide encoding an Ssa2 protein;
  b) a nucleic acid construct comprising a heterologous promoter operably linked to a polynucleotide encoding an Sse2 protein;
  c) nucleic acid construct comprising a heterologous promoter operably linked to a polynucleotide encoding an Hsc82 protein; and
  d) any combination of (a), (b), and (c).
 II) cultivating said host cell under conditions conducive for expression of the polypeptide of interest; and, optionally
 III) recovering the polypeptide of interest.

It will be evident to the person skilled in the art that the conditions conducive for expression of the polypeptide of interest should also be conducive for expression of the Ssa2 protein, the Sse2 protein, and/or the Hsc28 protein.

Preferably, the polypeptide of interest comprises an enzyme; preferably the enzyme is selected from the group consisting of hydrolase, isomerase, ligase, lyase, oxidoreductase, or transferase; more preferably an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, nuclease, oxidase, pectinolytic enzyme, peroxidase, phosphodiesterase, phytase, polyphenoloxidase, proteolytic enzyme, ribonuclease, transglutaminase, xylanase, and beta-xylosidase.

The fungal host cells are cultivated in a nutrient medium suitable for production of the polypeptide of interest using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide of interest is secreted into the nutrient medium, the polypeptide can be recovered directly from the medium. If the polypeptide of interest is not secreted, it can be recovered from cell lysates.

The polypeptide of interest may be detected using methods known in the art that are specific for said polypeptide. These detection methods include, but are not limited to, use of specific antibodies, formation of an enzyme product, or disappearance of an enzyme substrate. For example, an enzyme assay may be used to determine the activity of the polypeptide.

The polypeptide of interest may be recovered using methods known in the art. For example, the polypeptide of interest may be recovered from the nutrient medium by conventional procedures including, but not limited to, collection, centrifugation, filtration, extraction, spray-drying, evaporation, or precipitation. In one aspect, a fermentation broth comprising the polypeptide of interest is recovered.

The polypeptide of interest may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide of interest is not recovered, but rather a host cell of the present invention expressing the polypeptide of interest is used as a source of the polypeptide.

PREFERRED EMBODIMENTS

[1] A fungal host cell comprising in its genome at least one polynucleotide encoding a polypeptide of interest; and at least one nucleic acid construct selected from the group consisting of:
 a) a nucleic acid construct comprising a heterologous promoter operably linked to a polynucleotide encoding an Ssa2 protein;
 b) a nucleic acid construct comprising a heterologous promoter operably linked to a polynucleotide encoding an Sse2 protein;
 c) a nucleic acid construct comprising a heterologous promoter operably linked to a polynucleotide encoding an Hsc82 protein; and
 d) any combination of (a), (b), and (c).

[2] The fungal host cell according to embodiment 1, which comprises at least one polynucleotide encoding a polypeptide of interest; and
 i) at least one nucleic acid construct comprising a heterologous promoter operably linked to a polynucleotide encoding an Ssa2 protein AND at least one nucleic acid construct comprising a heterologous promoter operably linked to a polynucleotide encoding an Sse2 protein; OR
 ii) at least one nucleic acid construct comprising a heterologous promoter operably linked to a polynucleotide encoding an Ssa2 protein AND at least one nucleic acid construct comprising a heterologous promoter operably linked to a polynucleotide encoding an Hsc82 protein; OR
 iii) at least one nucleic acid construct comprising a heterologous promoter operably linked to a polynucleotide encoding an Sse2 protein AND at least one nucleic acid construct comprising a heterologous promoter operably linked to a polynucleotide encoding an Hsc82 protein; OR
 iv) at least one nucleic acid construct comprising a heterologous promoter operably linked to a polynucleotide encoding an Ssa2 protein AND at least one nucleic acid construct comprising a heterologous promoter operably linked to a polynucleotide encoding an Sse2 protein AND at least one nucleic acid construct comprising a heterologous promoter operably linked to a polynucleotide encoding an Hsc82 protein.

[3] The fungal host cell according to any of the preceding embodiments, said fungal host cell being a yeast host cell; preferably the yeast host cell is selected from the group consisting of *Candida*, *Hansenula*, *Kluyveromyces*, *Pichia*,

*Saccharomyces, Schizosaccharomyces,* and *Yarrowia* cell; more preferably the yeast host cell is selected from the group consisting of *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* and *Yarrowia lipolytica* cell.

[4] The fungal host cell according to embodiment 1, said fungal host cell being a filamentous fungal host cell; preferably the filamentous fungal host cell is selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* and *Trichoderma* cell; more preferably the filamentous fungal host cell is selected from the group consisting of *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* and *Trichoderma viride* cell; even more preferably the filamentous host cell is selected from the group consisting of *Aspergillus niger, Aspergillus oryzae, Fusarium venenatum,* and *Trichoderma reesei* cell; most preferably the filamentous fungal host cell is an *Aspergillus oryzae* cell.

[5] The fungal host cell according to any of the preceding embodiments, wherein the Ssa2 protein, the Sse2 protein, and/or the Hsc82 protein are, independently, homologous or heterologous to the fungal host cell.

[6] The fungal host cell according to any of the preceding embodiments, wherein the Ssa2 protein has at least 70% sequence identity to SEQ ID NO:2.

[7] The fungal host cell according to any of the preceding embodiments, wherein the polynucleotide encoding the Ssa2 protein has at least 70% sequence identity to SEQ ID NO:1.

[8] The fungal host cell according to any of the preceding embodiments, wherein the Sse2 protein has at least 70% sequence identity to SEQ ID NO:4.

[9] The fungal host cell according to any of the preceding embodiments, wherein the polynucleotide encoding the Sse2 protein has at least 70% sequence identity to SEQ ID NO:3.

[10] The fungal host cell according to any of the preceding embodiments, wherein the Hsc82 protein has at least 70% sequence identity to SEQ ID NO:6.

[11] The fungal host cell according to any of the preceding embodiments, wherein the polynucleotide encoding the Hsc82 protein has at least 70% sequence identity to SEQ ID NO:5.

[12] The fungal host cell according to any of the preceding embodiments, wherein the heterologous promoter(s) are, independently, selected from the group consisting of PamyB, Pgpd, Ptef1, PacuN, and PTAKA; preferably, the heterologous promoter is PamyB, Pgpd, or PTAKA.

[13] The fungal host cell according to any of the preceding embodiments, wherein the polypeptide of interest is a heterologous polypeptide.

[14] The fungal host cell according to any of the preceding embodiments, wherein the polypeptide of interest comprises an enzyme; preferably the enzyme is selected from the group consisting of hydrolase, isomerase, ligase, lyase, oxidoreductase, or transferase; more preferably an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, nuclease, oxidase, pectinolytic enzyme, peroxidase, phosphodiesterase, phytase, polyphenoloxidase, proteolytic enzyme, ribonuclease, transglutaminase, xylanase, and beta-xylosidase.

[15] The fungal host cell according to any of the preceding embodiments, wherein the polypeptide of interest is secreted; preferably the polypeptide of interest is secreted via the CPS pathway and/or the UPS pathway; most preferably the polypeptide of interest is secreted via the UPS pathway.

[16] The fungal host cell according to any of the preceding embodiments, wherein said host cell further comprises one or more additional polynucleotides encoding one or more additional polypeptides of interest.

[17] The fungal host cell according to embodiment 16, wherein the one or more additional polypeptides of interest are heterologous polypeptides.

[18] The fungal host cell according to any of embodiments 16-17, wherein the one or more additional polypeptides of interest comprise an enzyme; preferably the enzyme is selected from the group consisting of hydrolase, isomerase, ligase, lyase, oxidoreductase, or transferase; more preferably an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, nuclease, oxidase, pectinolytic enzyme, peroxidase, phosphodiesterase, phytase, polyphenoloxidase, proteolytic enzyme, ribonuclease, transglutaminase, xylanase, and beta-xylosidase.

[19] The fungal host cell according to any of embodiments 16-18, wherein the one or more additional polypeptides of interest are secreted; preferably the one or more additional polypeptides of interest are secreted via the CPS pathway and/or the UPS pathway; most preferably the one or more additional polypeptides of interest are secreted via the UPS pathway.

[20] A nucleic acid construct comprising:
   a) a heterologous promoter operably linked to a polynucleotide encoding an Ssa2 protein; OR
   b) a heterologous promoter operably linked to a polynucleotide encoding an Sse2 protein; OR
   c) a heterologus promoter operably linked to a polynucleotide encoding an Hsc82 protein.

[21] The nucleic acid construct according to embodiment 20, wherein the heterologous promoter is same or different heterologous promoter.

[22] The nucleic acid construct according to any of embodiments 20-21, wherein the heterologous promoter is selected from the group consisting of PamyB, Pgpd, Ptef1, PacuN, and PTAKA; preferably, the heterologous promoter is PamyB, Pgpd, or PTAKA.

[23] The nucleic acid construct according to any of embodiments 20-22, herein the Ssa2 protein has at least 70% sequence identity to SEQ ID NO:2.

[24] The nucleic acid construct according to any of embodiments 20-23, wherein the polynucleotide encoding the Ssa2 protein has at least 70% sequence identity to SEQ ID NO:1.

[25] The nucleic acid construct according to any of embodiments 20-24, wherein the Sse2 protein has at least 70% sequence identity to SEQ ID NO:4.

[26] The nucleic acid construct according to any of embodiments 20-25, wherein the polynucleotide encoding the Sse2 protein has at least 70% sequence identity to SEQ ID NO:3.

[27] The nucleic acid construct according to any of embodiments 20-26, wherein the Hsc82 protein has at least 70% sequence identity to SEQ ID NO:6.

[28] The nucleic acid construct according to any of embodiments 20-27, wherein the polynucleotide encoding the Hsc82 protein has at least 70% sequence identity to SEQ ID NO:5.

[29] An expression vector comprising a nucleic acid construct comprising:
   a) a heterologous promoter operably linked to a polynucleotide encoding an Ssa2 protein; OR
   b) a heterologous promoter operably linked to a polynucleotide encoding an Sse2 protein; OR
   c) a heterologus promoter operably linked to a polynucleotide encoding an Hsc82 protein.

[30] The expression vector according to embodiment 29, wherein the heterologous promoter is same or different heterologous promoter.

[31] The expression vector according to any of embodiments 29-30, wherein the heterologous promoter is selected from the group consisting of PamyB, Pgpd, Ptef1, PacuN, and PTAKA; preferably, the heterologous promoter is PamyB, Pgpd, or PTAKA.

[32] The expression vector according to any of embodiments 29-31, herein the Ssa2 protein has at least 70% sequence identity to SEQ ID NO:2.

[33] The expression vector according to any of embodiments 29-32, wherein the polynucleotide encoding the Ssa2 protein has at least 70% sequence identity to SEQ ID NO:1.

[34] The expression vector according to any of embodiments 29-33, wherein the Sse2 protein has at least 70% sequence identity to SEQ ID NO:4.

[35] The expression vector according to any of embodiments 29-34, wherein the polynucleotide encoding the Sse2 protein has at least 70% sequence identity to SEQ ID NO:3.

[36] The expression vector according to any of embodiments 29-35, wherein the Hsc82 protein has at least 70% sequence identity to SEQ ID NO:6.

[37] The expression vector according to any of embodiments 29-36, wherein the polynucleotide encoding the Hsc82 protein has at least 70% sequence identity to SEQ ID NO:5.

[38] A method for producing a polypeptide of interest, the method comprising:
   I) providing a fungal host cell comprising in its genome at least one polynucleotide encoding said polypeptide of interest; and at least one nucleic acid construct selected from the group consisting of:
      a) a nucleic acid construct comprising a heterologous promoter operably linked to polynucleotide encoding an Ssa2 protein;
      b) a nucleic acid construct comprising a heterologous promoter operably linked to a polynucleotide encoding an Sse2 protein;
      c) nucleic acid construct comprising a heterologous promoter operably linked to a polynucleotide encoding an Hsc82 protein; and
      d) any combination of (a), (b), and (c).
   II) cultivating said host cell under conditions conducive for expression of the polypeptide of interest; and, optionally
   III) recovering the polypeptide of interest.

[39] The method according to embodiment 38, wherein the fungal host cell comprises at least one polynucleotide encoding a polypeptide of interest; and
   i) at least one nucleic acid construct comprising a heterologous promoter operably linked to a polynucleotide encoding an Ssa2 protein AND at least one nucleic acid construct comprising a heterologous promoter operably linked to a polynucleotide encoding an Sse2 protein; OR
   ii) at least one nucleic acid construct comprising a heterologous promoter operably linked to a polynucleotide encoding an Ssa2 protein AND at least one nucleic acid construct comprising a heterologous promoter operably linked to a polynucleotide encoding an Hsc82 protein; OR
   iii) at least one nucleic acid construct comprising a heterologous promoter operably linked to a polynucleotide encoding an Sse2 protein AND at least one nucleic acid construct comprising a heterologous promoter operably linked to a polynucleotide encoding an Hsc82 protein; OR
   iv) at least one nucleic acid construct comprising a heterologous promoter operably linked to a polynucleotide encoding an Ssa2 protein AND at least one nucleic acid construct comprising a heterologous promoter operably linked to a polynucleotide encoding an Sse2 protein AND at least one nucleic acid construct comprising a heterologous promoter operably linked to a polynucleotide encoding an Hsc82 protein.

[40] The method according to any of embodiments 38-39, wherein the fungal host cell is a yeast host cell; preferably the yeast host cell is selected from the group consisting of *Candida, Hansenula, Kluyveromyces, Pichia, Saccharomyces, Schizosaccharomyces,* and *Yarrowia* cell; more preferably the yeast host cell is selected from the group consisting of *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* and *Yarrowia lipolytica* cell.

[41] The method according to any of embodiments 38-40, wherein the fungal host cell is a filamentous fungal host cell; preferably the filamentous fungal host cell is selected from the group consisting of *Acremonium, Aspergillus, Aureoba-* sidium, *Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, and *Trichoderma* cell; more preferably the filamentous fungal host cell is selected from the group consisting of *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, and *Trichoderma viride* cell; even more preferably the filamentous host cell is selected from the group consisting of *Aspergillus niger, Aspergillus oryzae, Fusarium venenatum*, and *Trichoderma reesei* cell; most preferably the filamentous fungal host cell is an *Aspergillus oryzae* cell.

[42] The method according to any of embodiment 38-41, wherein the Ssa2 protein, the Sse2 protein, and/or the Hsc82 protein are, independently, homologous or heterologous to the fungal host cell.

[43] The method according to any of embodiments 38-42, wherein the Ssa2 protein has at least 70% sequence identity to SEQ ID NO:2.

[44] The method according to any of embodiments 38-43, wherein the polynucleotide encoding the Ssa2 protein has at least 70% sequence identity to SEQ ID NO:1.

[45] The method according to any of embodiments 38-44, wherein the Sse2 protein has at least 70% sequence identity to SEQ ID NO:4.

[46] The method according to any of embodiments 38-45, wherein the polynucleotide encoding the Sse2 protein has at least 70% sequence identity to SEQ ID NO:3.

[47] The method according to any of embodiments 38-46, wherein the Hsc82 protein has at least 70% sequence identity to SEQ ID NO:6.

[48] The method according to any of embodiments 38-47, wherein the polynucleotide encoding the Hsc82 protein has at least 70% sequence identity to SEQ ID NO:5.

[49] The method according to any of embodiments 38-48, wherein the heterologous promoter(s) are, independently, selected from the group consisting of PamyB, Pgpd, Ptef1, PacuN, and PTAKA; preferably, the heterologous promoter is PamyB, Pgpd, or PTAKA.

[50] The method according to any of embodiments 38-49, wherein the polypeptide of interest is a heterologous polypeptide.

[51] The method according to any of embodiments 38-50, wherein the polypeptide of interest comprises an enzyme; preferably the enzyme is selected from the group consisting of hydrolase, isomerase, ligase, lyase, oxidoreductase, or transferase; more preferably an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, nuclease, oxidase, pectinolytic enzyme, peroxidase, phosphodiesterase, phytase, polyphenoloxidase, proteolytic enzyme, ribonuclease, transglutaminase, xylanase, and beta-xylosidase.

[52] The method according to any of embodiments 38-51, wherein the polypeptide of interest is secreted; preferably the polypeptide of interest is secreted via the CPS pathway and/or the UPS pathway; most preferably the polypeptide of interest is secreted via the UPS pathway.

[53] The method according to any of embodiments 38-52, wherein the fungal host cell further comprises one or more additional polynucleotides encoding one or more additional polypeptides of interest.

[54] The method according to embodiment 53, wherein the one or more additional polypeptides of interest are heterologous polypeptides.

[55] The method according to any of embodiments 53-54, wherein the one or more additional polypeptides of interest comprise an enzyme; preferably the enzyme is selected from the group consisting of hydrolase, isomerase, ligase, lyase, oxidoreductase, or transferase; more preferably an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, nuclease, oxidase, pectinolytic enzyme, peroxidase, phosphodiesterase, phytase, polyphenoloxidase, proteolytic enzyme, ribonuclease, transglutaminase, xylanase, and beta-xylosidase.

[56] The method according to any of embodiments 53-55, wherein the one or more additional polypeptides of interest are secreted; preferably the one or more additional polypeptides of interest are secreted via the CPS pathway and/or the UPS pathway; most preferably the one or more additional polypeptides of interest are secreted via the UPS pathway.

The present invention is further described by the following examples that should not be construed as limiting the scope of the invention.

EXAMPLES

Materials and Methods

General methods of PCR, cloning, ligation of nucleotides, etc. are well-known to a person skilled in the art and may for example be found in in "Molecular cloning: A laboratory manual", Sambrook et al. (1989), Cold Spring Harbor lab., Cold Spring Harbor, N.Y.; Ausubel, F. M. et al. (eds.); "Current protocols in Molecular Biology", John Wiley and Sons, (1995); Harwood, C. R., and Cutting, S. M. (eds.); "DNA Cloning: A Practical Approach, Volumes I and II", D. N. Glover ed. (1985); "Oligonucleotide Synthesis", M. J.

Gait ed. (1984); "Nucleic Acid Hybridization", B. D. Hames & S. J. Higgins eds (1985); "A Practical Guide To Molecular Cloning", B. Perbal, (1984).

Chemicals used as buffers and substrates were commercial products of at least reagent grade.

Aspergillus Transformation

Aspergillus transformation was done as described by Christensen et al. (Christensen et al. High level expression of recombinant genes in *Aspergillus oryzae. Biotechnology*, vol. 6, pp. 1419-1422, 1988). In short, *A. oryzae* mycelia were grown in a rich nutrient broth. The mycelia were separated from the broth by filtration. The enzyme preparation Glucanex® (Novozymes) was added to the mycelia in osmotically stabilizing buffer such as 1.2 M $MgSO_4$ buffered to pH 5.0 with sodium phosphate. The suspension was incubated for 60 minutes at 37° C. with agitation to produce protoplats. Protoplasts were filtered through miracloth to remove mycelial debris. The protoplasts were harvested and washed twice with STC (1.2 M sorbitol, 10 mM CaCl2, 10 mM Tris-HCl pH 7.5). Protoplasts were finally re-suspended in 200-1000 microl STC.

For transformation, 2 µg of plasmid DNA was added to 100 µl protoplast suspension and then 200 µl PEG solution (60% PEG 4000, 10 mM CaCl2, 10 mM Tris-HCl pH 7.5) was added and the mixture is incubated for 20 minutes at room temperature. The protoplasts were harvested and washed twice with 1.2 M sorbitol. The protoplasts were finally re-suspended 200 microl 1.2 M sorbitol. Transformants containing the BAR gene were selected for its ability to grow on minimal plates (D J Cove, 1966. *Biochem. Biophys. Acta*. 113:51-56) containing the antibiotic Basta (C J Thompson et al. Characterization of the herbicide-resistance gene bar from *Streptomyces hygroscopicus*. EMBO J, vol. 6, pp. 2519-2523, 1987). After 5-7 days of growth at 37° C., stable transformants appeared as vigorously growing and sporulating colonies. Transformants were purified through conidiation.

Sucrose Medium

1M Sucrose, 0.18 µM $Na_2B_4O_7$, 2.3 µM $CuSO_4$, 4.7 µM $FeSO_4$, 4.7 µM $MnSO_4$, 3.6 µM $Na_2MoO_4$, 45 µM $ZnSO_4$, 7 mM KCl, 4.3 mM $MgSO_4$, 11.2 mM $KH_2PO_4$.

Strain Cultivation

Shake flask containing 10 ml YPD medium (2 g/l yeast extract, 2 g/l peptone, and 2% glucose) were inoculated with spores from a transformant/heterokaryon or diploid strain and incubated at 30° C., 200 rpm for 4 days.

Bioreactor equipped with a temperature control system, pH control with ammonia water and phosphoric acid, dissolved oxygen probe to measure oxygen saturation through the entire fermentation were used for 1.5 L cultivation. Innoculation medium containing yeast extract (10 g/l), citric acid (1 g/l), sucrose (24 g/l), $(NH_4)_2SO_4$ (5 g/l), $MgSO_4$ (2 g/l), $KH_2PO_4$ (2 g/l), $K_2SO_4$ (2 g/l), sporemetal 1 (0.5 ml/l), pluronic (1 ml/l) and $FeSO_4$ (0.35 g/l) was used. Feeding medium containing maltose (feeding ramp), pluronic (1 ml/l) and citric acid (1 g/l) was used.

In-Fusion Cloning

In-Fusion Cloning was done using the In-Fusion cloning kit and manuals supplied by Clontech Laboratories, Inc.

SDS-PAGE

SDS gel used was Criterion™ XT precast gels, 10% Bis-Tris, from BIO-RAD and was run and stained with Coomassie blue as recommend by the manufactory.

Plasmids pAT1917 is described in Example 1 below.
pAT1818 is described in Example 2 below.
pAT2231 is described in Example 5 below.
pAT2303 is described in Example 7 below.
pAT2472 is described in Example 9 below.

Strains

BECh2 is described in WO 2000/39322.

DAu614 is derived from strain MT3830 (described in US 2011/0111453) and contains several copies of a lox1 expression cassette where the gene is under control of the PamyB promoter and an amdS selection marker (Kelly and Hynes, Transformation of *Aspergillus niger* by the amdS gene of *Aspergillus nidulans*, EMBO J 4:475-479, 1985).

BMcA041 is described in patent WO 2001/079465.

Example 1. Construction of Plasmid pAT1917 for Overexpression of ssa2

The purpose of this experiment was to construct a plasmid for *A. oryzae* Ssa2 chaperone over-expression that has a basta selection marker.

The plasmid pAT1917 (FIG. 1) was constructed by In-Fusion cloning. First, the expression cassette PTAKA-ssa2-Tssa2 was constructed by SOE-PCR amplification where the PTAKA DNA fragment was constructed using primers oAT3709 (SEQ ID NO:14) and oAT3702 (SEQ ID NO:7) using plasmid pJaL805 as template, and the ssa2-Tssa2 DNA fragment was constructed using primers oAT3703 (SEQ ID NO:8) and oAT3704 (SEQ ID NO:9) using genomic DNA from *A. oryzae* BECh2 as template. The expression cassette PTAKA-ssa2-Tssa2 was constructed by SOE-PCR amplification using oAT3709 (SEQ ID NO:14) and oAT3704 (SEQ ID NO:9) as primers and using PTAKA and ssa2-Tssa2 DNA fragments as templates. The resulting 2744 bp PCR fragment was cloned together with the 4519 bp NdeI/EcoRl fragment of plasmid pJaL680 by using In-Fusion cloning HD EcoDry cloning kit as described by the manufacturer (Clontech).

Example 2. Construction of Plasmid pAT1818 for Simultaneous Over-Expression of Ssa2 and Hsc82

The purpose of this experiment was to construct a plasmid for over-expression of both *A. oryzae* Ssa2 and Hsc82 chaperones using Basta selection (C J Thompson et al., vide supra).

Figure 2:
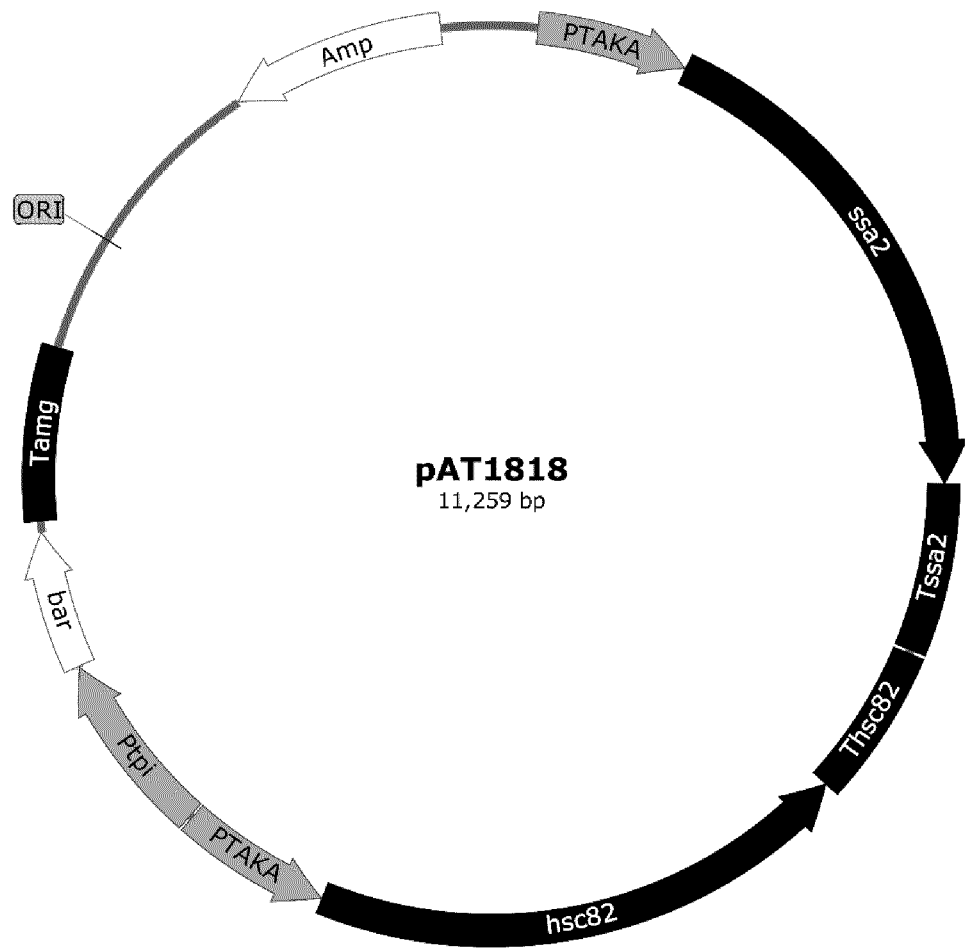
FIG. 2 shows plasmid pAT1818 for simultaneous overexpression of the ssa2 and hsc82 genes in *A. oryzae*.

Plasmid pAT1818 (FIG. 2) was constructed by In-Fusion cloning. First, the expression cassette $P_{TAKA}$-hsc82-Thsc82 was constructed by SOE-PCR amplification where the $P_{TAKA}$ DNA fragment was constructed using primers oAT3707 (SEQ ID NO:12) and oAT3708 (SEQ ID NO:13) using plasmid pJaL805 as template and the hsc82-Thsc82 DNA fragment was constructed using primers oAT3705 (SEQ ID NO:10) and oAT3706 (SEQ ID NO:11) using genomic DNA from *A. oryzae* BECh2 as template. The expression cassette $P_{TAKA}$-hsc82-Thsc82 was constructed by SOE-PCR amplification using oAT3705 (SEQ ID NO:10)

and oAT3707 (SEQ ID NO:12) as primers and using $P_{TAKA}$ and hsc82-Thsc82 DNA fragments as templates. The resulting 2815 bp PCR fragment was clone together with the $P_{TAKA}$-ssa2-Tssa2 fragment described in example 1 and 4519 bp NdeI/EcoRl fragment of plasmid pJaL680 by using In-Fusion cloning HD EcoDry cloning kit (Clontech) as described by the manufacturer.

Example 3. Increased Lipoxygenase Production by Overexpression of Ssa2 and Hsc82

The purpose of this experiment was to show that transformation with pAT1818, which leads to an over-expression of both chaperone homologs Ssa2 and Hsc82, increases the production of the soy lipoxygenase protein LOX1. LOX1 is a 839 amino acids enzyme with an estimated MW of 95 kDa.

Plasmid pAT1818 was therefore transformed into strain DAu614 that includes an expression cassette for lox1, and transformants were selected for its ability to grow on Sucrose medium containing the antibiotic Basta. The number of transformants was counted after 4 days at 37° C.

Figure 3:
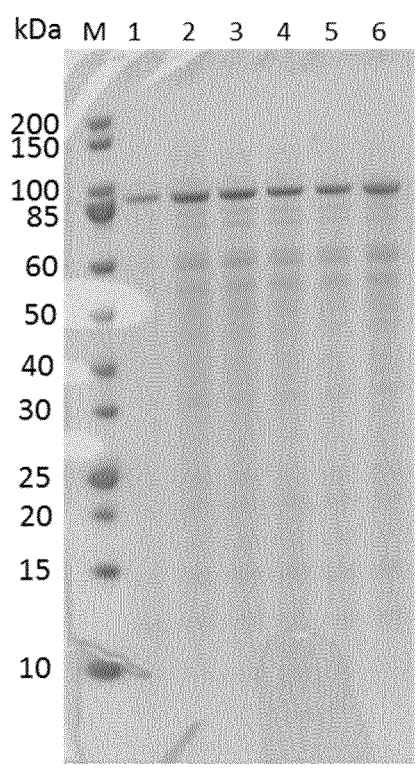
FIG. 3 shows SDS-PAGE depicting production of LOX in *A. oryzae* strains over-expressing the ssa2 gene. M: Molecular weights; lane 1: strain DAu614; lane 2: strain DAu614 pAT1818 #1; lane 3: strain DAu614 pAT1818 #2; lane 4: strain DAu614 pAT1818 #4; lane 5: strain DAu614 pAT1818 #7; lane 6: strain DAu614 pAT1818 #8.
Figure 4:
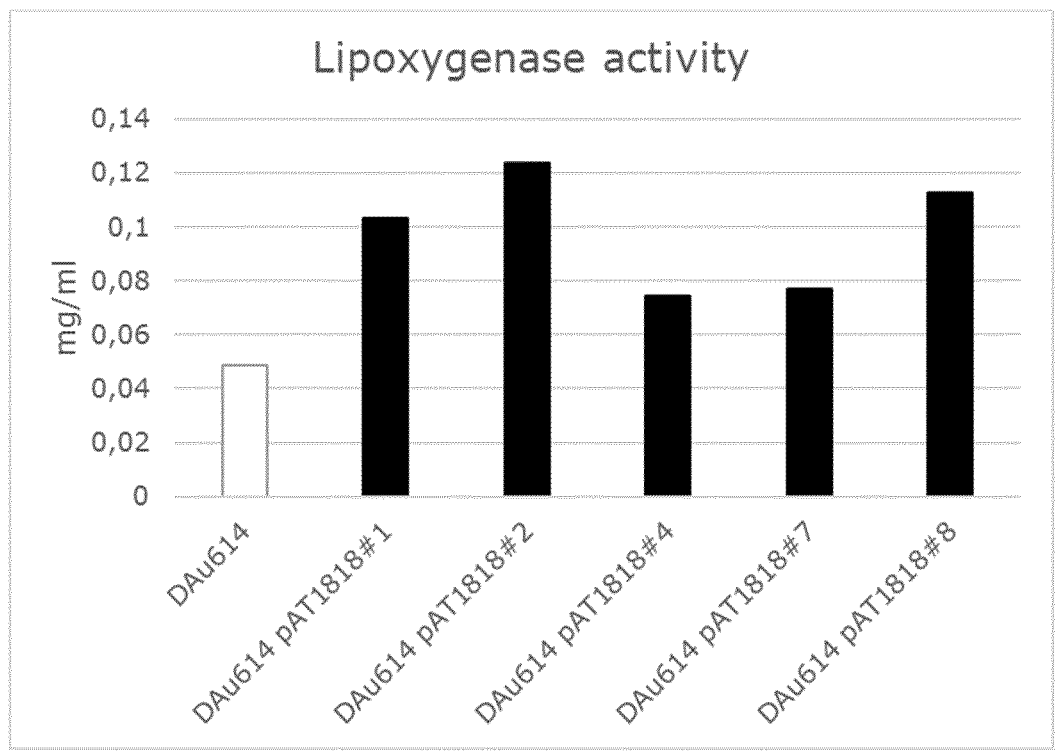
FIG. 4 shows lipoxygenase (LOX) activity in culture supernatants of *A. oryzae* strains over-expressing the ssa2 and hsc82 genes. Strain DAu614 is the reference strain producing LOX. Strains DAu614 pAT1818 are transformants containing vector pAT1818 described in Example 2.

Five transformants were spore isolated on Sucrose medium containing Basta. The five transformants was cultured in 10 ml YPD and supernatants were analyzed for lipoxygenase expression by SDS-PAGE (FIG. 3) and lipoxygenase activity assays (FIG. 4).

Example 4. Increased Haloperoxidase Production by Overexpression of Ssa2 and Hsc82

The purpose of this experiment was to show that transformation of pAT1818 or pAT1917 plasmids, which leads to an over-expression of both chaperones Ssa2 and Hsc82 or only Ssa2, increases the production of the haloperoxidase protein (HAP). HAP is a 600 aa protein with an estimated MW of 66 kD.

Plasmid was transformed into strain BMcA041, and transformants were selected for its ability to grow on Sucrose medium containing Basta. The number of transformants was counted after 4 days at 37° C.

Figure 5:
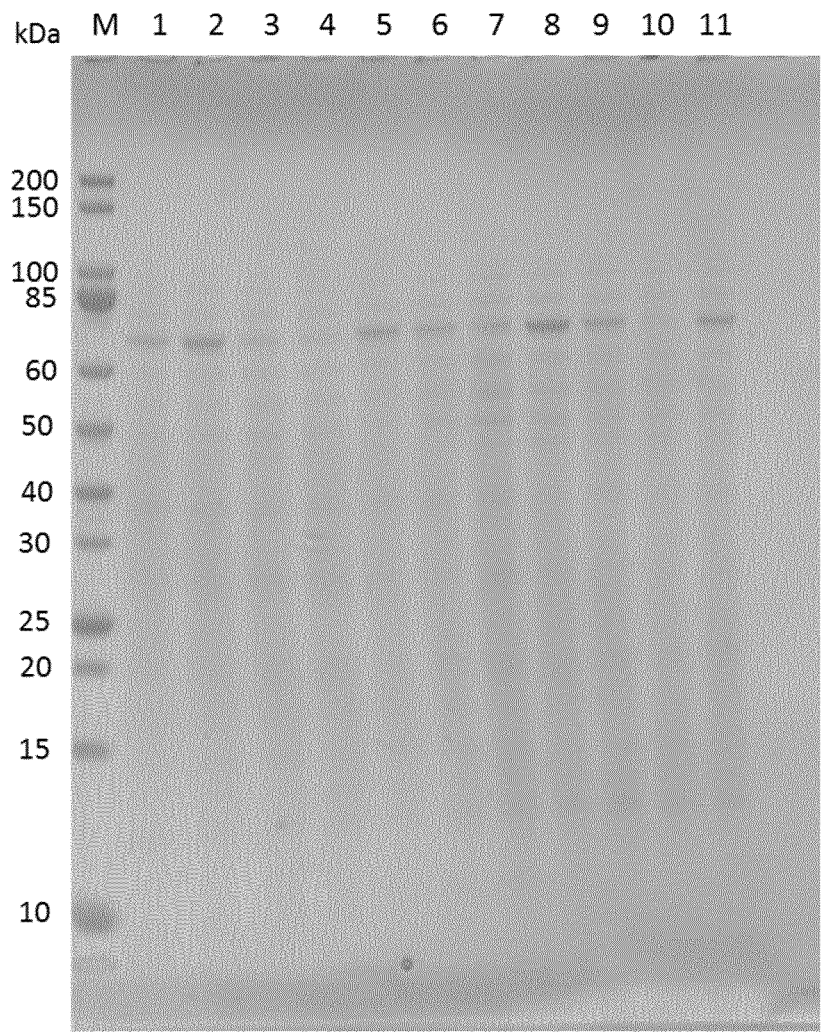
FIG. 5 shows SDS-PAGE depicting production of haloperoxidase in *A. oryzae* strains over-expressing the ssa2 gene alone or in combination with the hsc82 gene. M: Molecular weights; lane 1: strain BMcA041; lane 2: strain BMcA041 pAT1818 #1; lane 3: strain BMcA041 pAT1818 #2; lane 4: strain BMcA041 pAT1818 #3; lane 5: strain BMcA041 pAT1818 #4; lane 6: strain BMcA041 pAT1818 #5; lane 7: strain BMcA041 pAT1917 #1; lane 8: BMcA041 pAT1917 #2; lane 9: BMcA041 pAT1917 #3; lane 10: BMcA041 pAT1917 #4; lane 11: BMcA041 pAT1917 #5.
Figure 6:
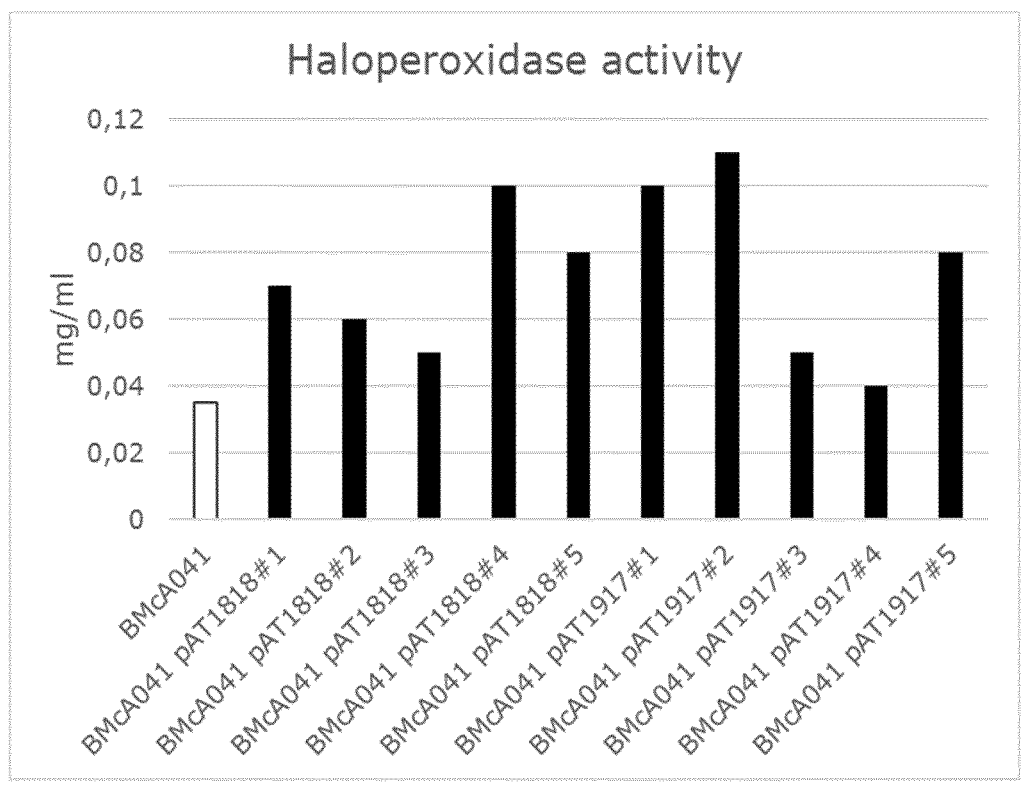
FIG. 6 shows haloperoxidase (HAP) activity in culture supernatants of *A. oryzae* strains over-expressing the ssa2 gene alone or in combination with the hsc82 gene. Strain BMcA041 is the reference strain producing HAP. Strains BMcA041 pAT1818 are transformants containing vector pAT1818 described in Example 2. Strains BMcA041 pAT1917 are transformants containing vector pAT1917 described in Example 1.

Five transformants from transformation pAT1818/BMcA041 were spore isolated on Sucrose medium containing Basta, and five transformants from transformation pAT1917/BMcA041 were spore isolated on Sucrose medium containing Basta. The ten above strains were cultured in 10 ml YPD and supernatants for lipoxygenase expression was analyzed by SDS-page (FIG. 5) and haloperoxidase activity assays (FIG. 6).

Example 5. Construction of Plasmid pAT2231 for Simultaneous Over-Expression of Ssa2 and Hsc82 Under GPD Promoter The purpose of this experiment was to construct a plasmid for over-expression of both *A. oryzae* Ssa2 and Hsc82 chaperones under the GPD promoter and using Basta selection (C J Thompson et al., vide supra).

Figure 7:
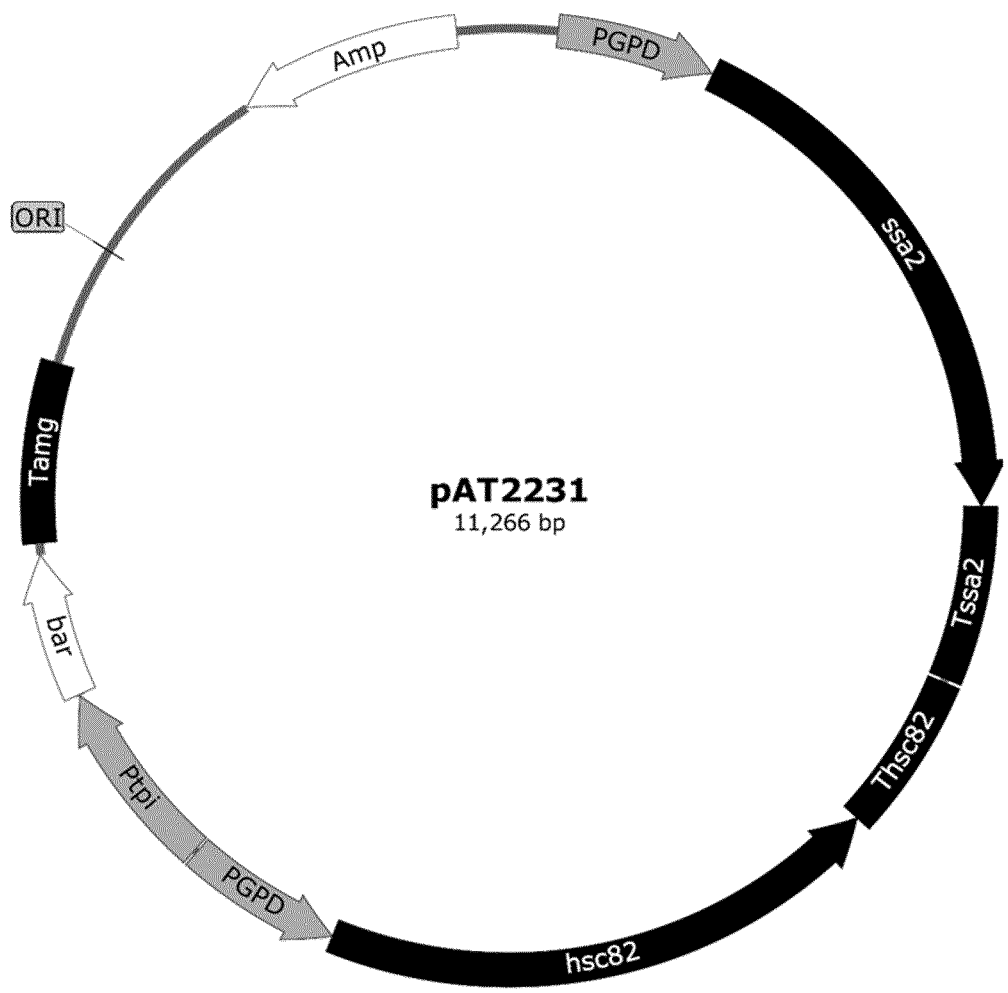
FIG. 7 shows plasmid pAT2231 for simultaneous overexpression of the ssa2 and hsc82 genes under the GPD promoter in *A. oryzae*.

The plasmid pAT2231 (FIG. 7) was constructed by In-Fusion cloning. First, the expression cassette $P_{GPD}$-ssa2-Tssa2 was constructed by SOE-PCR amplification where the $P_{GPD}$ DNA fragment was constructed using primers oAT3713 (SEQ ID NO:15) and oAT3714 (SEQ ID NO:16) using plasmid pRung81 as template, and the ssa2-Tssa2 DNA fragment was constructed using primers oAT3715 (SEQ ID NO:17) and oAT3716 (SEQ ID NO:18) using genomic DNA from *A. oryzae* BECh2 as template. The expression cassette $P_{GPD}$-ssa2-Tssa2 was constructed by SOE-PCR amplification using oAT3713 (SEQ ID NO:15) and oAT3704 (SEQ ID NO:9) as primers and using $P_{GPD}$ and ssa2-Tssa2 DNA fragments as templates, resulting in a 3362 bp PCR fragment. Second, the expression cassette $P_{GPD}$-hsc82-Thsc82 was constructed by SOE-PCR amplification where the $P_{GPD}$ DNA fragment was constructed using primers oAT3717 (SEQ ID NO:19) and oAT3718 (SEQ ID NO:20) using plasmid pRung81 as template and the hsc82-Thsc82 DNA fragment was constructed using primers oAT3705 (SEQ ID NO:10) and oAT3716 (SEQ ID NO:18) using genomic DNA from *A. oryzae* BECh2 as template. The expression cassette $P_{GPD}$-hsc82-Thsc82 was constructed by SOE-PCR amplification using oAT3705 (SEQ ID NO:10) and oAT3718 (SEQ ID NO:20) as primers and using $P_{GPD}$ and hsc82-Thsc82 DNA fragments as templates. The resulting 3428 bp PCR fragment was clone together with the $P_{GPD}$-ssa2-Tssa2 fragment described previously and 4519 bp NdeI/EcoRl fragment of plasmid pJaL680 by using In-Fusion cloning HD EcoDry cloning kit (Clontech) as described by the manufacturer.

Example 6. Increased Lipoxygenase Production by Overexpression of Ssa2 and Hsc82

The purpose of this experiment was to show that transformation with pAT2231, which leads to an over-expression of both chaperone homologs Ssa2 and Hsc82 under the GPD promoter, increases the production of the soy lipoxygenase protein LOX1. LOX1 is a 839 amino acids enzyme with an estimated MW of 95 kDa.

Plasmid pAT2231 was therefore transformed into strain DAu614 that includes an expression cassette for lox1, and transformants were selected for its ability to grow on Sucrose medium containing the antibiotic. Strain AT2441 was selected for its increased soy lipoxygenase protein LOX1 production from Example 5.

Figure 8:
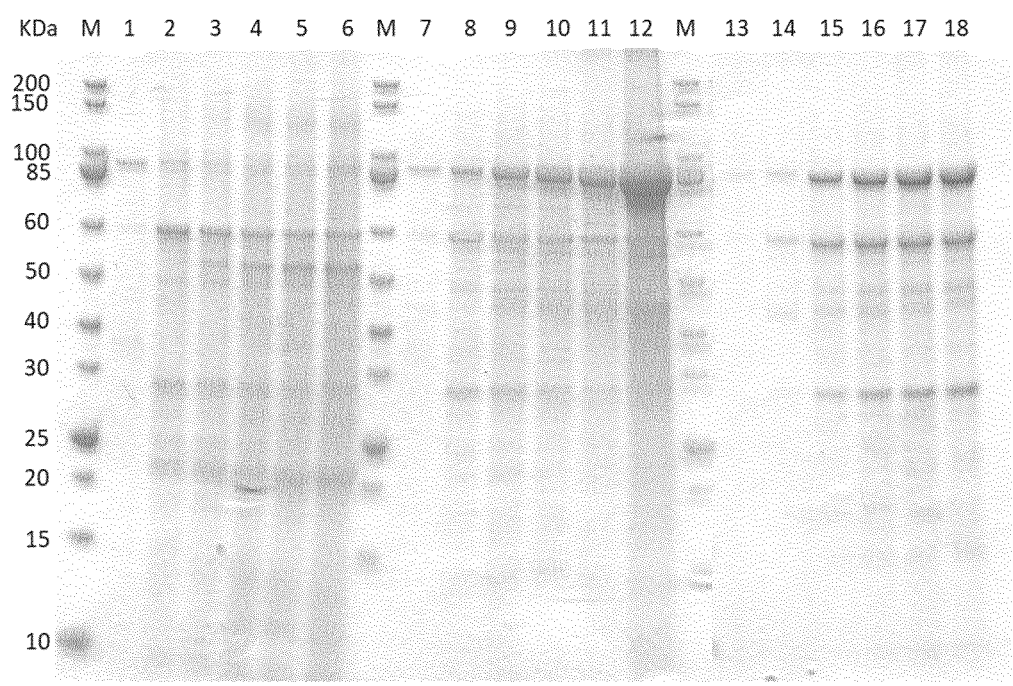
FIG. 8 shows SDS-PAGE depicting large-scale production of LOX in *A. oryzae* strains DAu614, AT2335 and AT2441 over-expressing the ssa2 and hsc82 genes. M: Molecular weights; Lane 1: strain DAu614 at day 1; lane 2: strain DAu614 at day 2; lane 3: strain DAu614 at day 4; lane 4: strain DAu614 at day 5; lane 5: strain DAu614 at day 6; lane 6: strain DAu614 at day 7; lane 7: strain AT2335 at day 1; lane 8: strain AT2335 at day 2; lane 9: strain AT2335 at day 4; lane 10: strain AT2335 at day 5; lane 11: strain AT2335 at day 6; lane 12: strain AT2335 at day 7; lane 13: strain AT2441 at day 1; lane 14: strain AT2441 at day 2; lane 15: strain AT2441 at day 4; lane 16: strain AT2441 at day 5; lane 17: strain AT2441 at day 6; lane 18: strain AT21441 at day 7.
Figure 9:
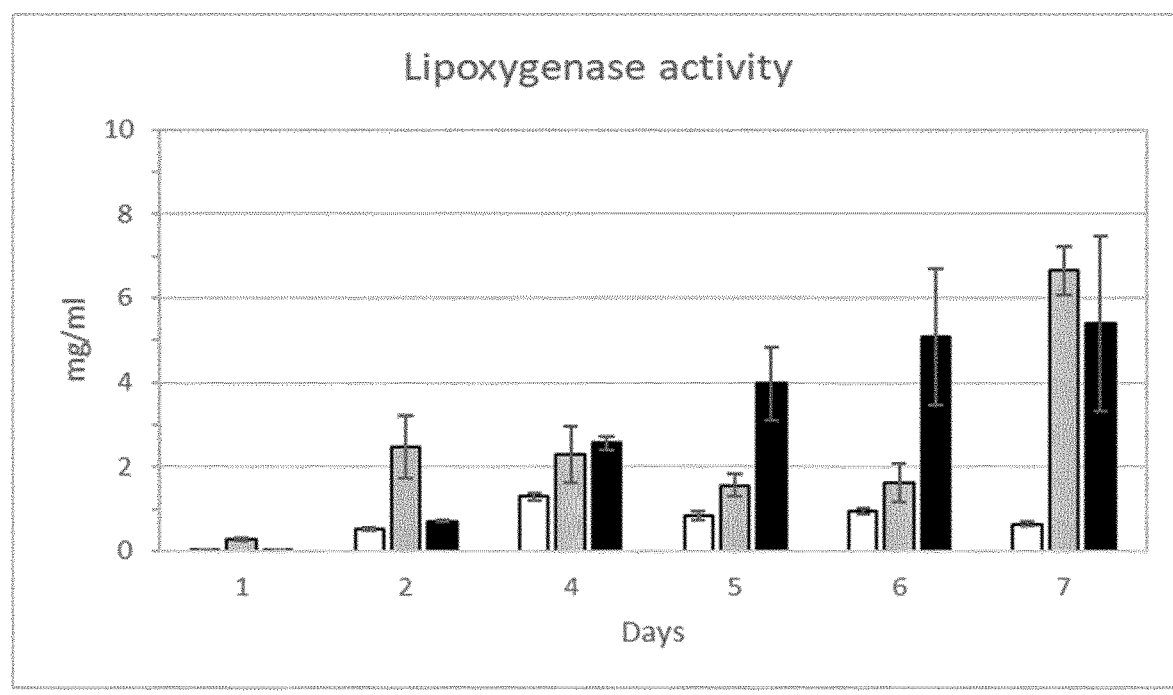
FIG. 9 shows lipoxygenase (LOX) activity in culture supernatants of *A. oryzae* strains DAu614 (white bars), AT2335 (grey bars) and AT2441 (black bars) over-expressing the ssa2 and hsc82 genes. Strain DAu614 is the reference strain producing LOX. Strains AT2335 and AT2441 are transformants containing either vector pAT1818 described in Example 2 or vector pAT2231 described in Example 5.
Figure 10:
FIG. 10 shows plasmid pAT2303 for simultaneous overexpression of the ssa2 and sse2 genes under the TAKA promoter in *A. oryzae*.

Strain AT2335 was selected for its increased soy lipoxygenase protein LOX1 production from Example 2. Strains DAu614, AT2335 and AT2441 were cultured in 1.5 L bioreactor and supernatants were analyzed for lipoxygenase expression by SDS-PAGE (FIG. 8) and lipoxygenase activity assays (FIG. 9).

Example 7. Construction of Plasmid pAT2303 for Simultaneous Over-Expression of Ssa2 and Sse2 Under TAKA Promoter The purpose of this experiment was to construct a plasmid for over-expression of both *A. oryzae* Ssa2 and Sse2 chaperones under the TAKA promoter and using Basta selection (C J Thompson et al., vide supra).

The plasmid pAT2303 (FIG. 7) was constructed by In-Fusion cloning. First, the expression cassette $P_{TAKA}$-ssa2-Tssa2 was constructed by SOE-PCR amplification where the $P_{TAKA}$ DNA fragment was constructed using primers oAT3709 (SEQ ID NO:14) and oAT3702 (SEQ ID NO:7) using plasmid pJaL805 as template, and the ssa2-Tssa2 DNA fragment was constructed using primers oAT3703 (SEQ ID NO:8) and oAT3704 (SEQ ID NO:9) using genomic DNA from *A. oryzae* BECh2 as template. The expression cassette $P_{TAKA}$-ssa2-Tssa2 was constructed by SOE-PCR amplification using oAT3709 (SEQ ID NO:14) and oAT3704 (SEQ ID NO:9) as primers and using $P_{TAKA}$ and ssa2-Tssa2 DNA fragments as templates, resulting in a 3362 bp PCR fragment. Second, the expression cassette $P_{TAKA}$-sse2-Tsse2 was constructed by SOE-PCR amplification where the $P_{TAKA}$ DNA fragment was constructed using primers oAT3707 (SEQ ID NO:12) and oAT3708 (SEQ ID NO:13) using plasmid pJaL805 as template and the sse2-Tsse2 DNA fragment was constructed using primers oAT3719 (SEQ ID NO:21) and oAT3720 (SEQ ID NO:22) using genomic DNA from *A. oryzae* BECh2 as template. The expression cassette $P_{TAKA}$-sse2-Tsse2 was constructed by SOE-PCR amplification using oAT3707 (SEQ ID NO:12) and oAT3719 (SEQ ID NO:21) as primers and using $P_{TAKA}$ and sse2-Tsse2 DNA fragments as templates. The resulting 4203 bp PCR fragment was clone together with the $P_{TAKA}$-ssa2-Tssa2 fragment described previously and 4519 bp NdeI/EcoRI fragment of plasmid pJaL680 by using In-Fusion cloning HD EcoDry cloning kit (Clontech) as described by the manufacturer.

Example 8. Increased Lipoxygenase Production by Overexpression of Ssa2 and Sse2

The purpose of this experiment was to show that transformation with pAT2303, which leads to an over-expression of both chaperone homologs Ssa2 and Sse2 under the TAKA promoter, increases the production of the soy lipoxygenase protein LOX1. LOX1 is a 839 amino acids enzyme with an estimated MW of 95 kDa.

Plasmid pAT2303 was therefore transformed into strain DAu614 that includes an expression cassette for lox1, and transformants were selected for its ability to grow on Sucrose medium containing the antibiotic. Strain AT2442 was selected for its increased soy lipoxygenase protein LOX1 production from Example 7.

Figure 11:
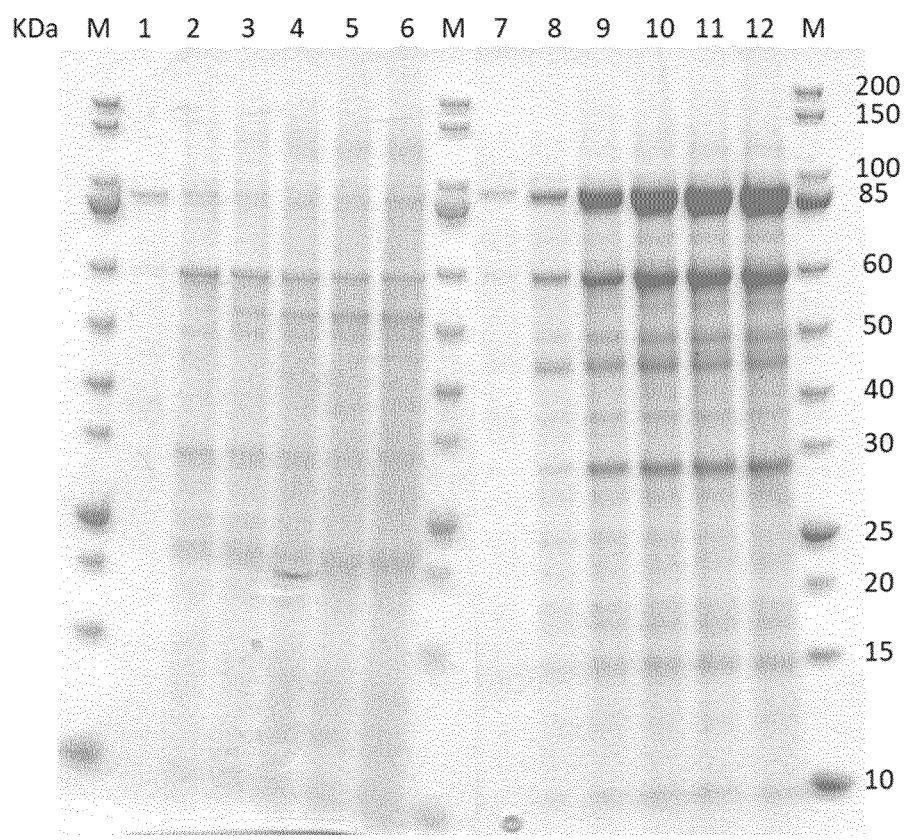
FIG. 11 shows SDS-PAGE depicting large-scale production of LOX in *A. oryzae* strains DAu614 and AT2442 over-expressing the ssa2 and sse2 genes. M: Molecular weights; Lane 1: strain DAu614 at day 1; lane 2: strain DAu614 at day 2; lane 3: strain DAu614 at day 4; lane 4: strain DAu614 at day 5; lane 5: strain DAu614 at day 6; lane 6: strain DAu614 at day 7; lane 7: strain AT2442 at day 1; lane 8: strain AT2442 at day 2; lane 9: strain AT2442 at day 4; lane 10: strain AT2442 at day 5; lane 11: strain AT2442 at day 6; lane 12: strain AT2442 at day 7.
Figure 12:
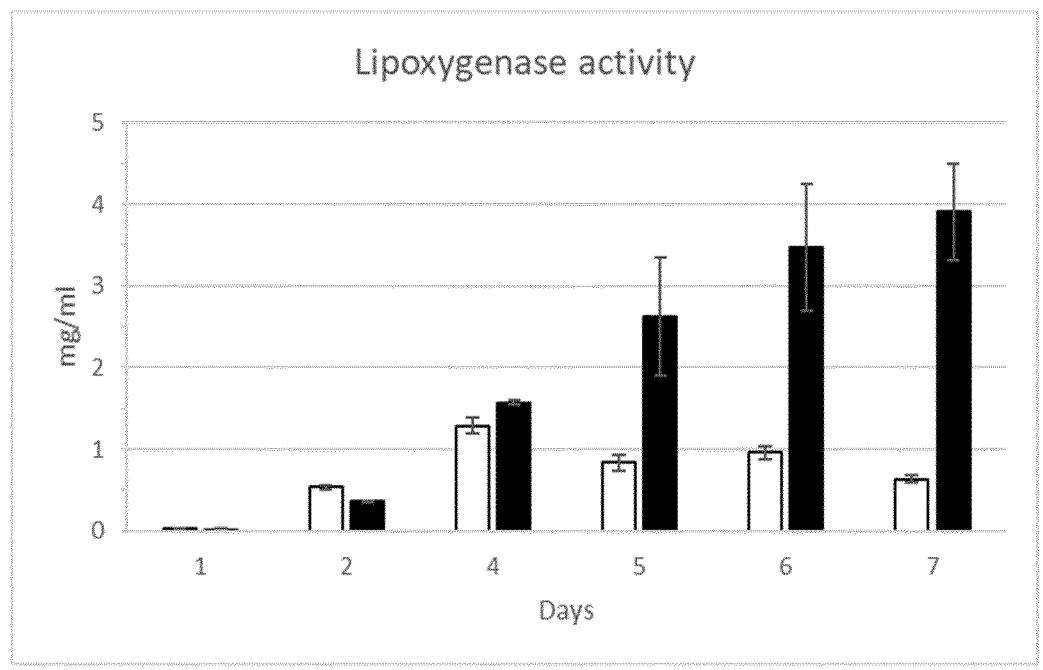
FIG. 12 shows lipoxygenase (LOX) activity in culture supernatants of *A. oryzae* strains DAu614 (white bars) and AT2442 (black bars) over-expressing the ssa2 and sse2 genes. Strain DAu614 is the reference strain producing LOX. Strain AT2442 is a transformant containing vector pAT2303 described in Example 7.

Strains DAu614 and AT2442 were cultured in 1.5 L bioreactor and supernatants were analyzed for lipoxygenase expression by SDS-PAGE (FIG. 11) and lipoxygenase activity assays (FIG. 12).

Example 9. Construction of Plasmid pAT2472 for Simultaneous Over-Expression of Ssa2 and Sse2 Under TAKA Promoter and Hsc82 Under GPD Promoter The purpose of this experiment was to construct a plasmid for over-expression of *A. oryzae* Ssa2 and Sse2 chaperones under the TAKA promoter and Hsc82 chaperone under the GPD promoter and using Basta selection (C J Thompson et al., vide supra).

Figure 13:
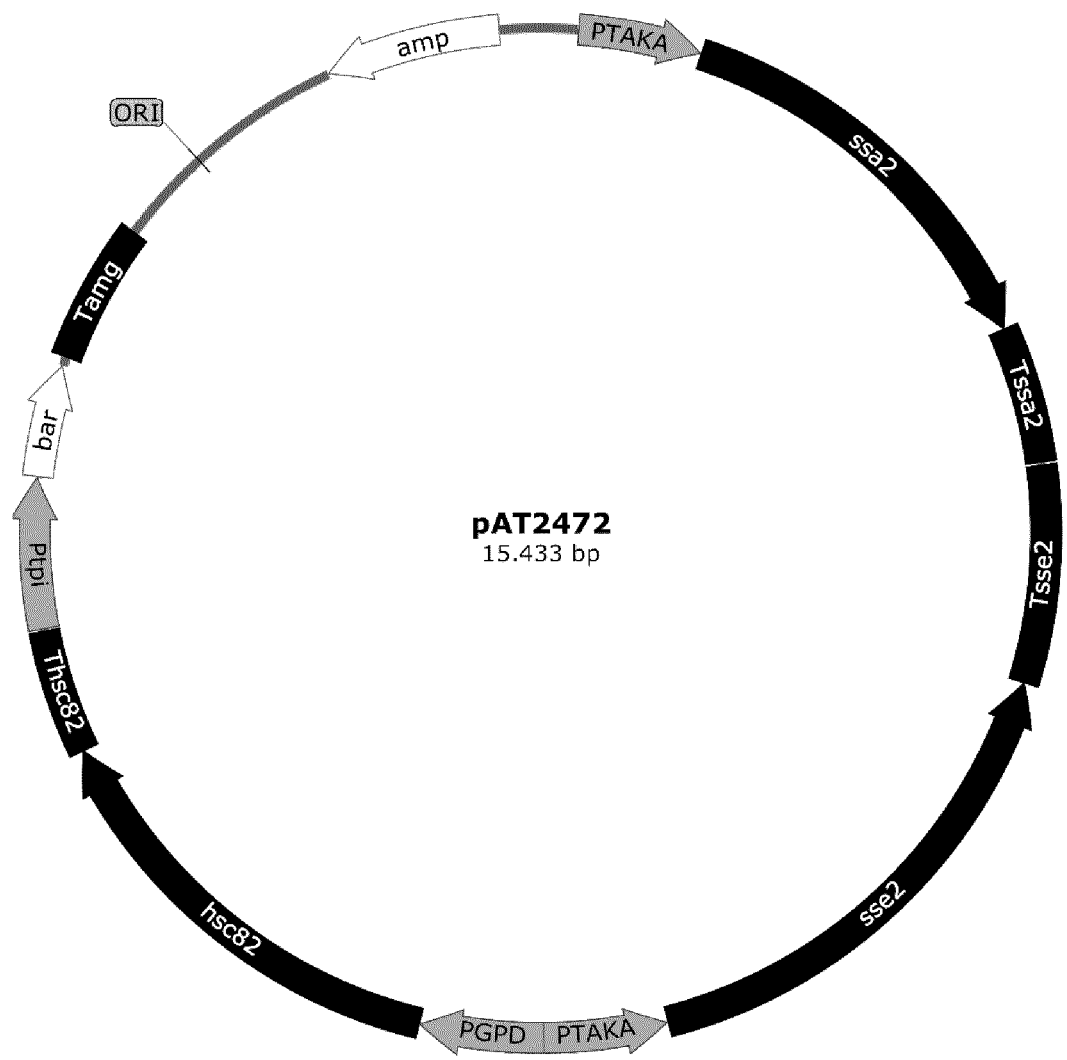
FIG. 13 shows plasmid pAT2472 for simultaneous overexpression of the ssa2 and sse2 genes under the TAKA promoter and the hsc82 gene under the GPD promoter in *A. oryzae*.

The plasmid pAT2472 (FIG. 13) was constructed by In-Fusion cloning. First, the expression cassette $P_{TAKA}$-ssa2-Tssa2 was constructed by SOE-PCR amplification where the $P_{TAKA}$ DNA fragment was constructed using primers oAT3709 (SEQ ID NO:14) and oAT3702 (SEQ ID NO:7) using plasmid pJaL805 as template, and the ssa2-Tssa2 DNA fragment was constructed using primers oAT3703 (SEQ ID NO:8) and oAT3704 (SEQ ID NO:9) using genomic DNA from *A. oryzae* BECh2 as template. The expression cassette $P_{TAKA}$-ssa2-Tssa2 was constructed by SOE-PCR amplification using oAT3709 (SEQ ID NO:14) and oAT3704 (SEQ ID NO:9) as primers and using $P_{TAKA}$ and ssa2-Tssa2 DNA fragments as templates, resulting in a 3362 bp PCR fragment. Second, the expression cassette $P_{TAKA}$-sse2-Tsse2 was constructed by SOE-PCR amplification where the $P_{TAKA}$ DNA fragment was constructed using primers oAT3725 (SEQ ID NO:23) and oAT3708 (SEQ ID NO:13) using plasmid pJaL805 as template and the sse2-Tsse2 DNA fragment was constructed using primers oAT3719 (SEQ ID NO:21) and oAT3720 (SEQ ID NO:22) using genomic DNA from *A. oryzae* BECh2 as template. The expression cassette $P_{TAKA}$-sse2-Tsse2 was constructed by SOE-PCR amplification using oAT3725 (SEQ ID NO:23) and oAT3719 (SEQ ID NO:21) as primers and using $P_{TAKA}$ and sse2-Tsse2 DNA fragments as templates, resulting in a 4202 bp PCR fragment. Third, the expression cassette $P_{GPD}$-hsc82-Thsc82 was constructed by SOE-PCR amplification where the $P_{GPD}$ DNA fragment was constructed using primers oAT3717 (SEQ ID NO:19) and oAT3726 (SEQ ID NO:24) using plasmid pRung81 as template and the hsc82-Thsc82 DNA fragment was constructed using primers oAT3727 (SEQ ID NO:25) and oAT3716 (SEQ ID NO:18) using genomic DNA from *A. oryzae* BECh2 as template. The expression cassette $P_{GPD}$-hsc82-Thsc82 was constructed by SOE-PCR amplification using oAT3726 (SEQ ID NO:24) and oAT3727 (SEQ ID NO:25) as primers and using $P_{GPD}$ and hsc82-Thsc82 DNA fragments as templates. The resulting 3428 bp PCR fragment was clone together with the $P_{TAKA}$-ssa2-Tssa2 fragment and $P_{TAKA}$-sse2-Tsse2 fragment described previously and 4519 bp NdeI/EcoRI fragment of plasmid pJaL680 by using In-Fusion cloning HD EcoDry cloning kit (Clontech) as described by the manufacturer.

Example 10. Increased Lipoxygenase Production by Overexpression of Ssa2, Sse2 and Hsc82

The purpose of this experiment was to show that transformation with pAT2472, which leads to an over-expression of both chaperone homologs Ssa2 and Sse2 under the TAKA promoter and homolog Hsc82 under the GPD promoter, increases the production of the soy lipoxygenase protein LOX1. LOX1 is a 839 amino acids enzyme with an estimated MW of 95 kDa.

Plasmid pAT2472 was therefore transformed into strain DAu614 that includes an expression cassette for lox1, and transformants were selected for its ability to grow on Sucrose medium containing the antibiotic. Strain AT2710 was selected for its increased soy lipoxygenase protein LOX1 production from Example 9.

Figure 14:
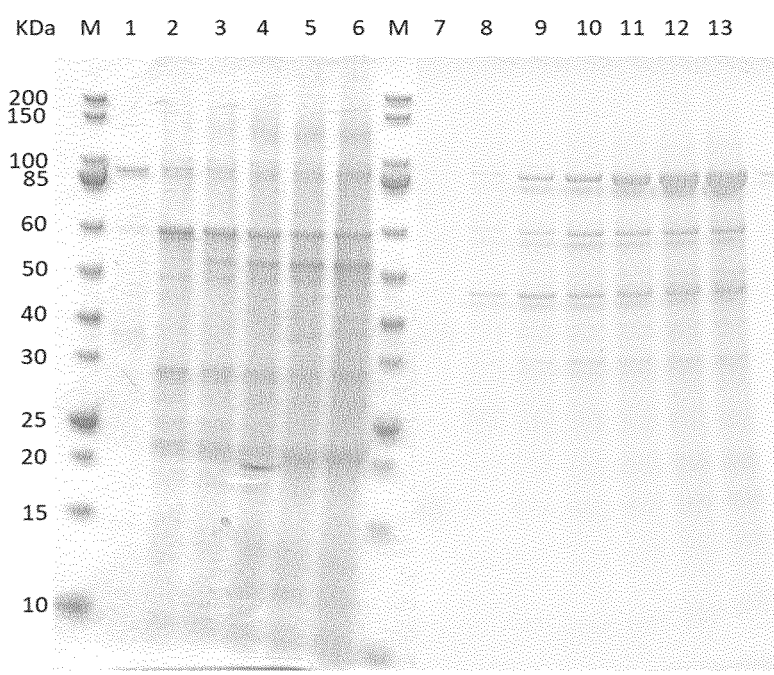
FIG. 14 shows SDS-PAGE depicting large-scale production of LOX in *A. oryzae* strains DAu614 and AT2710 over-expressing the ssa2, sse2 and hsc82 genes. M: Molecular weights; Lane 1: strain DAu614 at day 1; lane 2: strain DAu614 at day 2; lane 3: strain DAu614 at day 4; lane 4: strain DAu614 at day 5; lane 5: strain DAu614 at day 6; lane 6: strain DAu614 at day 7; lane 7: strain AT2710 at day 1; lane 8: strain AT2710 at day 2; lane 9: strain AT2710 at day 3; lane 10: strain AT2710 at day 4; lane 11: strain AT2710 at day 5; lane 12: strain AT2710 at day 6; lane 13: strain AT2710 at day 7.
Figure 15:
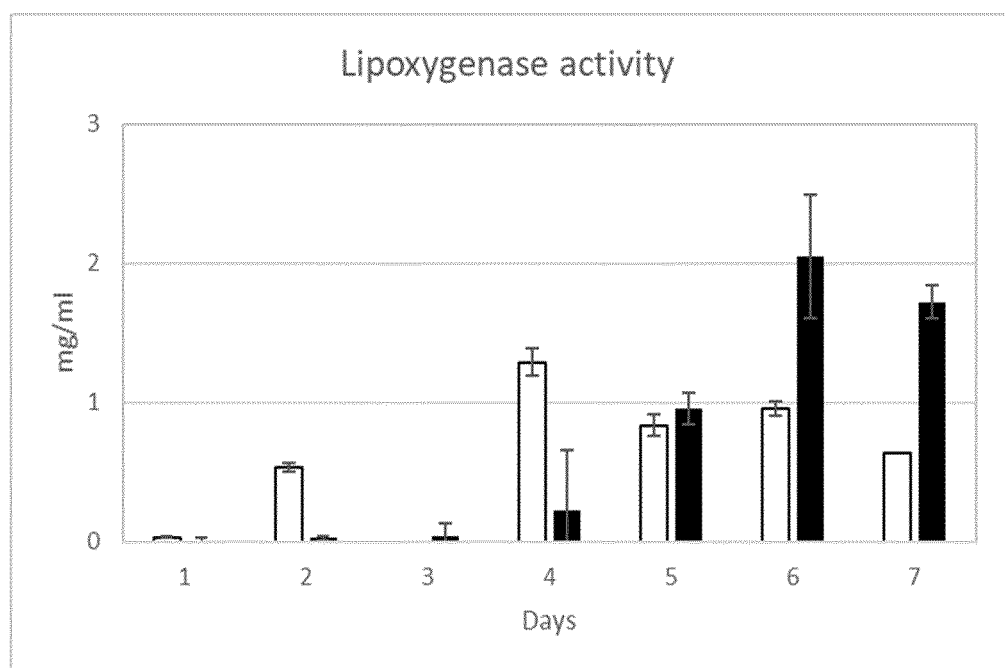
FIG. 15 shows lipoxygenase (LOX) activity in culture supernatants of *A. oryzae* strains DAu614 (white bars) and AT2710 (black bars) over-expressing the ssa2, sse2 and hsc82 genes. Strain DAu614 is the reference strain producing LOX. Strain AT2710 is a transformant containing vector pAT2472 described in Example 9.

Strains DAu614 and AT2710 were cultured in 1.5 L bioreactors and supernatants were analyzed for lipoxygenase expression by SDS-PAGE (FIG. 14) and lipoxygenase activity assays (FIG. 15).

The invention claimed is:

1. An *Aspergillus* host cell comprising in its genome at least one polynucleotide encoding a soy lipoxygenase protein (LOX1), at least one nucleic acid construct comprising a heterologous promoter operably linked to a polynucleotide encoding an Ssa2 protein, and at least one nucleic acid construct comprising a heterologous promoter operably linked to a polynucleotide encoding an Hsc82 protein.

2. The *Asperqillus* host cell according to claim 1, wherein the Ssa2 protein, and/or the Hsc82 protein are, independently, homologous or heterologous to the *Aspergillus* host cell.

3. The *Asperqillus* host cell according to claim 1, wherein the Ssa2 protein has at least 90% sequence identity to SEQ ID NO: 2.

4. The *Asperqillus* host cell according to claim 1, wherein the polynucleotide encoding the Ssa2 protein has at least 90% sequence identity to SEQ ID NO: 1.

5. The *Aspergillus* host cell according to claim 1, wherein the Hsc82 protein has at least 90% sequence identity to SEQ ID NO: 6.

6. The *Asperqillus* host cell according to claim 1, wherein the polynucleotide encoding the Hsc82 protein has at least 90% sequence identity to SEQ ID NO: 5.

7. The *Asperqillus* host cell according to claim 1, wherein the heterologous promoter(s) are, independently, selected from the group consisting of PamyB, Pgpd, Ptef1, PacuN, and PTAKA.

8. The *Aspergillus* host cell according to claim 1, wherein said host cell further comprises one or more additional polynucleotide encoding one or more additional polypeptide of interest.

9. The *Aspergillus* host cell according to claim 1, wherein said *Aspergillus* host cell is an *Aspergillus niger* cell or an *Aspergillus oryzae* cell.

10. The *Aspergillus* host cell according to claim 1, wherein said host is an *Aspergillus oryzae* cell.

11. The *Aspergillus* host cell according to claim 1, wherein the Ssa2 protein has at least 90% sequence identity to SEQ ID NO: 2 and the Hsc82 protein at least 90% sequence identity to SEQ ID NO: 6.

12. The *Aspergillus* host cell according to claim 1, wherein the Ssa2 protein has at least 95% sequence identity to SEQ ID NO: 2 and the Hsc82 protein at least 95% sequence identity to SEQ ID NO: 6.

13. The *Aspergillus* host cell according to claim 1, wherein the Ssa2 protein has at least 98% sequence identity to SEQ ID NO: 2 and the Hsc82 protein at least 98% sequence identity to SEQ ID NO: 6.

14. The *Aspergillus* host cell according to claim 1, wherein the polynucleotide encoding the Ssa2 protein has at least 90% sequence identity to SEQ ID NO: 1 and the polynucleotide encoding the Hsc82 protein has at least 90% sequence identity to SEQ ID NO: 5.

15. The *Aspergillus* host cell according to claim 1, wherein the polynucleotide encoding the Ssa2 protein has at least 95% sequence identity to SEQ ID NO: 1 and the polynucleotide encoding the Hsc82 protein has at least 95% sequence identity to SEQ ID NO: 5.

16. The *Aspergillus* host cell according to claim 1, wherein the polynucleotide encoding the Ssa2 protein has at least 98% sequence identity to SEQ ID NO: 1 and the polynucleotide encoding the Hsc82 protein has at least 98% sequence identity to SEQ ID NO: 5.

17. A method for producing a soy lipoxygenase protein (LOX1), the method comprising:
   I) providing the *Aspergillus* host cell of claim 1; and
   II) cultivating said host cell under conditions conducive for expression of the soy lipoxygenase protein (LOX1).

18. The method of claim 17, further comprising:
   III) recovering the polypeptide of interest.

* * * * *